(12) United States Patent
Auguste et al.

(10) Patent No.: US 12,383,553 B2
(45) Date of Patent: *Aug. 12, 2025

(54) METHOD FOR DETECTING OR TREATING TRIPLE NEGATIVE BREAST CANCER

(71) Applicant: Children's Medical Center Corporation, Boston, MA (US)

(72) Inventors: Debra Auguste, Briarcliff Manor, NY (US); Marsha A. Moses, Brookline, MA (US); Peng Guo, Natick, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/091,145

(22) Filed: Dec. 29, 2022

(65) Prior Publication Data
US 2023/0248721 A1 Aug. 10, 2023

Related U.S. Application Data

(63) Continuation of application No. 15/127,240, filed as application No. PCT/US2015/023078 on Mar. 27, 2015, now abandoned.

(60) Provisional application No. 61/970,943, filed on Mar. 27, 2014.

(51) Int. Cl.
| | |
|---|---|
| A61K 39/00 | (2006.01) |
| A61K 9/14 | (2006.01) |
| A61K 31/191 | (2006.01) |
| A61K 31/429 | (2006.01) |
| A61K 31/4365 | (2006.01) |
| A61K 31/4965 | (2006.01) |
| A61K 39/395 | (2006.01) |
| A61K 47/54 | (2017.01) |
| C12Q 1/6886 | (2018.01) |
| G01N 33/574 | (2006.01) |

(52) U.S. Cl.
CPC ............ *A61K 31/4965* (2013.01); *A61K 9/14* (2013.01); *A61K 31/191* (2013.01); *A61K 31/429* (2013.01); *A61K 31/4365* (2013.01); *A61K 47/555* (2017.08); *C12Q 1/6886* (2013.01); *G01N 33/57415* (2013.01); *A61K 2121/00* (2013.01); *C12Q 2600/158* (2013.01); *G01N 2333/70525* (2013.01)

(58) Field of Classification Search
None
See application file for complete search history.

(56) References Cited

U.S. PATENT DOCUMENTS

| | | | |
|---|---|---|---|
| 5,284,931 A | | 2/1994 | Springer et al. |
| 5,288,854 A | | 2/1994 | Diamond et al. |
| 5,475,091 A | * | 12/1995 | Springer .......... C07K 14/70525 |
| | | | 530/388.22 |
| 5,626,870 A | | 5/1997 | Minshipouri et al. |
| 6,203,793 B1 | * | 3/2001 | Lipsky ............... C07K 16/2821 |
| | | | 424/153.1 |
| 6,316,024 B1 | | 11/2001 | Allen et al. |
| 6,569,451 B1 | | 5/2003 | Bednarski et al. |
| 9,388,249 B2 | | 7/2016 | Sugioka et al. |
| 9,737,492 B2 | | 8/2017 | Mao et al. |
| 10,092,188 B2 | | 10/2018 | Jaffer et al. |
| 10,421,758 B2 | | 9/2019 | Chiosis et al. |
| RE48,787 E | | 10/2021 | Adair et al. |
| 11,260,132 B2 | * | 3/2022 | Moses .................... A61K 9/127 |
| 2002/0071843 A1 | | 6/2002 | Bednarski et al. |
| 2004/0013720 A1 | | 1/2004 | Ellens et al. |
| 2007/0111331 A1 | | 5/2007 | Hong et al. |
| 2007/0280948 A1 | | 12/2007 | Williams et al. |
| 2008/0187595 A1 | | 8/2008 | Jordan et al. |
| 2009/0186078 A1 | | 7/2009 | Kliche et al. |
| 2010/0008978 A1 | | 1/2010 | Drummond et al. |
| 2010/0209490 A1 | | 8/2010 | Morita et al. |
| 2010/0285002 A1 | | 11/2010 | Peer et al. |
| 2011/0244048 A1 | | 10/2011 | Amiji et al. |
| 2013/0034548 A1 | | 2/2013 | Moyo et al. |
| 2013/0064763 A1 | | 3/2013 | Abulrob et al. |
| 2014/0127187 A1 | | 5/2014 | Niitsu et al. |
| 2014/0127287 A1 | | 5/2014 | Xiong et al. |
| 2014/0314666 A1 | | 10/2014 | Muro Galindo et al. |
| 2015/0064265 A1 | | 3/2015 | Fahmy et al. |
| 2017/0173005 A1 | | 6/2017 | Auguste et al. |

(Continued)

FOREIGN PATENT DOCUMENTS

| | | |
|---|---|---|
| EP | 2468775 A1 | 6/2012 |
| WO | WO 1991/16928 A1 | 11/1991 |

(Continued)

OTHER PUBLICATIONS

Cybulsky MI, Fries JW, Williams AJ, et al. Alternative splicing of human VCAM-1 in activated vascular endothelium. Am J Pathol 1991; 138: 815-20. (Year: 1991).*
Rosette et al. Role of ICAM1 in invasion of human breast cancer cells. Carcinogenesis, 25(5):943-950, 2005. (Year: 2005).*
Chavez et al. Triple Negative Breast Cancer Cell Lines: One Tool in the Search for Better Treatment of Triple Negative Breast Cancer. Breast Dis. 2010 ; 32(1-2): 35-48. (Year: 2010).*
Schlesinger and Bendas. Vascular cell adhesion molecule-1 (VCAM-1)-An increasing insight into its role in tumorigenicity and metastasis. IJC, 136(11):2504-2514, 2015 (Year: 2015).*

(Continued)

*Primary Examiner* — Maher M Haddad
(74) *Attorney, Agent, or Firm* — Wolf, Greenfield & Sacks, P.C.

(57) ABSTRACT

A method of detecting triple negative breast cancer (TNBC) is provided. Overexpression of ICAM-1 is linked to an increased risk of TNBC. A composition of matter is also provided that binds an anti-ICAM~1 antibody to a nanoparticle. The composition may be used as an imaging agent and/or a therapeutic targeting agent. A therapeutically active molecule may be bound to the composition to provide targeted therapy.

5 Claims, 18 Drawing Sheets

(56) References Cited

U.S. PATENT DOCUMENTS

| | | |
|---|---|---|
| 2020/0085972 A1 | 3/2020 | Moses et al. |
| 2021/0113466 A1 | 4/2021 | Moses et al. |
| 2022/0280653 A1 | 9/2022 | Moses et al. |
| 2024/0148888 A1 | 5/2024 | Guo et al. |

FOREIGN PATENT DOCUMENTS

| | | | |
|---|---|---|---|
| WO | WO 1998/016201 A1 | 4/1998 | |
| WO | WO 1998/016202 A1 | 4/1998 | |
| WO | WO 02/36073 A2 | 5/2002 | |
| WO | WO 2006/116107 A2 | 11/2006 | |
| WO | WO 2007/127219 A2 | 11/2007 | |
| WO | WO 2007/127221 A2 | 11/2007 | |
| WO | WO 2007/127272 A2 | 11/2007 | |
| WO | WO 2009/026328 A2 | 2/2009 | |
| WO | WO 2012/007516 A1 | 1/2012 | |
| WO | WO 2012/106559 A1 | 8/2012 | |
| WO | WO 2012/155048 A1 | 11/2012 | |
| WO | WO 2014/046630 A1 | 3/2014 | |
| WO | WO 2015/066535 A1 | 5/2015 | |
| WO | WO 2015/089419 A2 | 6/2015 | |
| WO | WO 2015/148971 A2 | 10/2015 | |
| WO | WO 2015/191693 A2 | 12/2015 | |
| WO | WO 2016/064882 A1 | 4/2016 | |
| WO | WO 2017/223135 A1 | 12/2017 | |
| WO | WO 2022/182743 A1 | 9/2022 | |

OTHER PUBLICATIONS

Nizamutdinova et al. Tanshinone I suppresses growth and invasion of human breast cancer cells, MDA-MB-231, through regulation of adhesion molecules. Carcinogenesis vol. 29 No. 10 pp. 1885-1892, 2008. (Year: 2008).*

[No Author Listed]Enlimomab Acute Stroke Trial Investigators. Use of anti-ICAM-1 therapy in ischemic stroke: results of the Enlimomab Acute Stroke Trial. Neurology. Oct. 23, 2001;57(8):1428-34.

Buitrago et al., Intercellular adhesion molecule-1 (ICAM-1) is upregulated in aggressive papillary thyroid carcinoma. Ann Surg Oncol. Mar. 2012;19(3):973-80.

Cahall et al., A Quantitative Perspective on Surface Marker Selection for the Isolation of Functional Tumor Cells. Breast Cancer (Auckl). Jul. 27, 2015;9(Suppl 1):1-11.

Carter et al., Antibody-drug conjugates for cancer therapy. Cancer J. May-Jun. 2008;14(3):154-69.

Chen et al., Mechanism of apoptosis induced by urosolic acid in gastric carcinoma BGC-823 cells. Wuhan Daxue Xuebao, Yixueban. 2006;27(3):299-302. English Abstract Only.

Chen et al., Targeted Delivery of CRISPR/Cas9-Mediated Cancer Gene Therapy via Liposome-Templated Hydrogel Nanoparticles. Adv Funct Mater. Dec. 8, 2017; 27(46): 1-18.

Chen, Small-molecule delivery by nanoparticles for anticancer therapy. Trends Mol Med. Dec. 2010;16(12):594-602.

Chittasupho et al., ICAM-1 targeting of doxorubicin-loaded PLGA nanoparticles to lung epithelial cells. Eur J Pharm Sci. May 12, 2009;37(2):141-50.

Claesson-Welsh et al., Permeability of the Endothelial Barrier: Identifying and Reconciling Controversies. Trends Mol Med. Apr. 2021;27(4):314-331.

Clauss et al., A permissive role for tumor necrosis factor in vascular endothelial growth factor-induced vascular permeability. Blood. Mar. 1, 2001;97(5):1321-9.

Crown et al., Emerging targeted therapies in triple-negative breast cancer. Ann Oncol. Aug. 2012;23 Suppl 6:vi56-65.

Dan et al., Binding, transcytosis and biodistribution of anti-PECAM-1 iron oxide nanoparticles for brain-targeted delivery. PLoS One. Nov. 20, 2013;8(11):e81051.

Ding et al., A non-cationic nucleic acid nanogel for the delivery of the CRISPR/Cas9 gene editing tool. Nanoscale. 2019;11:17211-17215.

Ducry et al., Antibody-drug conjugates: linking cytotoxic payloads to monoclonal antibodies. Bioconjug Chem. Jan. 2010;21(1):5-13.

Grijalvo et al., Biodegradable liposome-encapsulated hydrogels for biomedical applications: a marriage of convenience. Biomater Sci. Apr. 2016;4(4):555-74.

Gunawan et al., Complementary targeting of liposomes to IL-1α and TNF-α activated endothelial cells via the transient expression of VCAM1 and E-selectin. Biomaterials. Dec. 2011;32(36):9848-53.

Guo et al., Abstract 4410: An ICAM-1-targeted, Lcn2 siRNA-encapsulating liposome as a potent anti-angiogenic agent for triple-negative breast cancer. In: Proceedings of the 106th Annual Meeting of the American Association for Cancer Research; Apr. 18-22, 2015; Philadelphia, PA. Philadelphia (PA): AACR; Cancer Res 2015;75(15 Suppl):Abstract nr 4410.

Guo et al., ICAM-1 as a molecular target for triple negative breast cancer. Proc Natl Acad Sci U S A. Oct. 14, 2014;111(41):14710-5.

Guo et al., ICAM-1-Targeted, Lcn2 siRNA-Encapsulating Liposomes are Potent Anti-angiogenic Agents for Triple Negative Breast Cancer. Theranostics. Jan. 1, 2016;6(1):1-13.

Guo et al., Inhibiting metastatic breast cancer cell migration via the synergy of targeted, pH-triggered siRNA delivery and chemokine axis blockade. Mol Pharm. Mar. 3, 2014;11(3):755-65.

Guo et al., Therapeutic genome editing of triple-negative breast tumors using a noncationic and deformable nanolipogel. Proc Natl Acad Sci U S A. Sep. 10, 2019;116(37):18295-18303. doi: 10.1073/pnas.1904697116. Epub Aug. 26, 2019.

Hendriks et al., Impact of tumor HER2/ERBB2 expression level on HER2-targeted liposomal doxorubicin-mediated drug delivery: multiple low-affinity interactions lead to a threshold effect. Mol Cancer Ther. Sep. 2013;12(9):1816-28.

Huang et al., Casein-coated iron oxide nanoparticles for high MRI contrast enhancement and efficient cell targeting. ACS Appl Mater Interfaces. Apr. 2013;5(11):4632-4639.

Jung et al., Expression of intercellular adhesion molecule-1 and e-selectin in gastric cancer and their clinical significance. J Gastric Cancer. Sep. 2012;12(3):140-8.

Kelly et al., Human colon cancer cells express ICAM-1 in vivo and support LFA-1-dependent lymphocyte adhesion in vitro. Am J Physiol. Dec. 1992;263(6 Pt 1):G864-70.

Liu et al., Self-assembled nanoparticles based on a carboxymethylcellulose-ursolic acid conjugate for anticancer combination therapy. RSC Advances. 2017;7:36256.

Manikwar et al., Utilization of I-domain of LFA-1 to Target Drug and Marker Molecules to Leukocytes. Theranostics. 2011;1:277-89. doi: 10.7150/thno/v01p0277. Epub May 10, 2011.

Maruo et al., ICAM-1 expression and the soluble ICAM-1 level for evaluating the metastatic potential of gastric cancer. Int J Cancer. 2002;100:486-490.

Mastrobattista et al., Cellular uptake of liposomes targeted to intercellular adhesion molecule-1 (ICAM-1) on bronchial epithelial cells. Biochim Biophys Acta. Jul. 15, 1999;1419(2):353-63.

Morral-Ruiz et al., Multifunctional polyurethane-urea nanoparticles to target and arrest inflamed vascular environment: a potential tool for cancer therapy and diagnosis. J Control Release. 2013;171(2):163-171.

Muro et al., Control of intracellular trafficking of ICAM-1-targeted nanocarriers by endothelial Na+/H+ exchanger proteins. Am J Physiol Lung Cell Mol Physiol. May 2006;290(5):L809-17. doi: 10.1152/ajplung.00311.2005. Epub Nov. 18, 2005.

Muro et al., Lysosomal enzyme delivery by ICAM-1-targeted nanocarriers bypassing glycosylation- and clathrin-dependent endocytosis. Mol Ther. Jan. 2006;13(1):135-41. doi: 10.1016/j.ymthe.2005.07.687. Epub Sep. 8, 2005.

Muro et al., Slow intracellular trafficking of catalase nanoparticles targeted to ICAM-1 protects endothelial cells from oxidative stress. Am J Physiol Cell Physiol. 2003;285:C1339-C1347.

Murphy et al., Targeted nanogels: a versatile platform for drug delivery to tumors. Mol Cancer Ther. Jun. 2011;10(6):972-82. doi: 10.1158/1535-7163.MCT-10-0729. Epub Apr. 25, 2011.

Oh et al., Endocytosis and exocytosis of nanoparticles in mammalian cells. Int J Nanomedicine. May 6, 2014;9 Suppl 1(Suppl 1):51-63.

(56) References Cited

OTHER PUBLICATIONS

Pannier et al., Surface- and hydrogel-mediated delivery of nucleic acid nanoparticles. Methods Mol Biol. 2013;948:149-69.
Papademetriou et al., Comparative binding, endocytosis, and biodistribution of antibodies and antibody-coated carriers for targeted delivery of lysosomal enzymes to ICAM-1 versus transferrin receptor. J Inherit Metab Dis. May 2013;36(3):467-477. doi: 10.1007/s10545-012-9534-6.
Park et al., Characterization of radioligand binding to a transmembrane receptor reconstituted into Lipobeads. FEBS Lett. Jun. 4, 2004;567(2-3):344-8. doi: 10.1016/j.febslet.2004.03.124.
Rosette et al., Role of ICAM1 in invasion of human breast cancer cells. Carcinogenesis. Mar. 17, 2005;26(5):943-950.
Senter, Potent antibody drug conjugates for cancer therapy. Curr Opin Chem Biol. Jun. 2009;13(3):235-44.
Shimoyama et al., Overexpression of intercellular adhesion molecule-1 (ICAM-1) in pancreatic adenocarcinoma in comparison with normal pancreas. Pancreas. Mar. 1997;14(2):181-6.
Song et al., Development and characterisation of ursolic acid nanocrystals without stabiliser having improved dissolution rate and in vitro anticancer activity. AAPS PharmSciTech. Feb. 2014;15(1):11-19.
Sughrue et al., Anti-adhesion molecule strategies as potential neuroprotective agents in cerebral ischemia: a critical review of the literature. Inflamm Res. Oct. 2004;53(10):497-508.
Taniguchi et al., Effects of the anti-ICAM-1 monoclonal antibody on dextran sodium sulphate-induced colitis in rats. J Gastroenterol Hepatol. Sep. 1998;13(9):945-9.
Usami et al., Intercellular adhesion molecule-1 (ICAM-1) expression correlates with oral cancer progression and induces macrophage/cancer cell adhesion. Int J Cancer. Aug. 1, 2013;133(3):568-78.
Villanueva et al., Microbubbles targeted to intercellular adhesion molecule-1 bind to activated coronary artery endothelial cells. Circulation. Jul. 7, 1998;98(1):1-5.
Wang et al., In Vivo Delivery Systems for Therapeutic Genome Editing. Int J Mol Sci. Apr. 27, 2016;17(5):626. doi: 10.3390/ijms17050626.
Xavier et al., Ursolic acid induces cell death and modulates autophagy through JNK pathway in apoptosis-resistant colorectal cancer cells. J Nutr Biochem. Apr. 2013;24(4):706-12.
Xu et al., Antibody conjugated magnetic iron oxide nanoparticles for cancer cell separation in fresh whole blood. Biomaterials. Dec. 2011;32(36):9758-9765.
Yu et al., Improved delivery of Cas9 protein/gRNA complexes using lipofectamine CRISPRMAX. Biotechnol Lett. Jun. 2016;38(6):919-29.
Zhang et al., Anti-ICAM-1 antibody reduces ischemic cell damage after transient middle cerebral artery occlusion in the rat. Neurology. Sep. 1994;44(9):1747-51.
Zhang et al., Delivery of ursolic acid (UA) in polymeric nanoparticles effectively promotes the apoptosis of gastric cancer cells through enhanced inhibition of cyclooxygenase 2 (COX-2). Int J Pharm. 2013;441:261-268.
Zhang et al., PLGA nanoparticle—peptide conjugate effectively targets intercellular cell-adhesion molecule-1. Bioconjug Chem. Jan. 2008;19(1):145-52.
[No Author Listed], Definition of "oligonucleotide" from biologyonline. com. Accessed as available Feb. 20, 2024 from < https://web.biology.com/dictionary/oligonucleotide>.
[No Author Listed], Definition of "polynucleotide" from biologyonline. com. Accessed as available Feb. 2, 20240 from <https://web.biology.com/dictionary/polynucleotide>.
Bhowmick et al., Effect of flow on endothelial endocytosis of nanocarriers targeted to ICAM-1. J Control Release. Feb. 10, 2012;157(3):485-92. doi: 10.1016/j.jconrel.2011.09.067. Epub Sep. 16, 2011. Author Manuscript, 19 pages.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Goel et al., Plasticity within the antigen-combining site may manifest as molecular mimicry in the humoral immune response. J Immunol. Dec. 15, 2004;173(12):7358-67. doi: 10.4049/jimmunol. 173.12.7358.
Kanyavuz et al., Breaking the law: unconventional strategies for antibody diversification. Nat Rev Immunol. Jun. 2019;19(6):355-368. doi: 10.1038/s41577-019-0126-7.
Lloyd et al., Modelling the human immune response: performance of a 1011 human antibody repertoire against a broad panel of therapeutically relevant antigens. Protein Eng Des Sel. Mar. 2009;22(3):159-68.
Machado et al., Encapsulation of DNA in macroscopic and nanosized calcium alginate gel particles. Langmuir. Dec. 23, 2013;29(51):15926-35. doi: 10.1021/la4032927. Epub Dec. 11, 2013.
Murciano et al., ICAM-directed vascular immunotargeting of antithrombotic agents to the endothelial luminal surface. Blood. May 15, 2003;101(10):3977-84. doi: 10.1182/blood-2002-09-2853. Epub Jan. 16, 2003.
Nograles et al., Formation and characterization of pDNA-loaded alginate microspheres for oral administration in mice. J Biosci Bioeng. Feb. 2012;113(2):133-40. doi: 10.1016/j.jbiosc.2011.10.003. Epub Nov. 16, 2011.
Elstrodt et al., BRCA1 mutation analysis of 41 human breast cancer cell lines reveals three new deleterious mutants. Cancer Res. Jan. 1, 2006;66(1):41-5. doi: 10.1158/0008-5472.CAN-05-2853.
Pisani et al., Neutral Liposomes and DNA Transfection. Excerpt from Non-Viral Gene Therapy, Chapter 14. Ed. Xubo Yuan. InTech. Nov. 2011:319-48.
Rae et al., MDA-MB-435 cells are derived from M14 melanoma cells—a loss for breast cancer, but a boon for melanoma research. Breast Cancer Res Treat. Jul. 2007;104(1):13-9. doi: 10.1007/s10549-006-9392-8. Epub Sep. 27, 2006.
Xiong et al., Cationic liposomes as gene delivery system: transfection efficiency and new application. Pharmazie. Mar. 2011;66(3):158-64.
Brooks et al., The antitumor activity of an anti-CD54 antibody in SCID mice xenografted with human breast, prostate, non-small cell lung, and pancreatic tumor cell lines. Int J Cancer. Nov. 15, 2008;123(10):2438-45. doi: 10.1002/ijc.23793.

\* cited by examiner

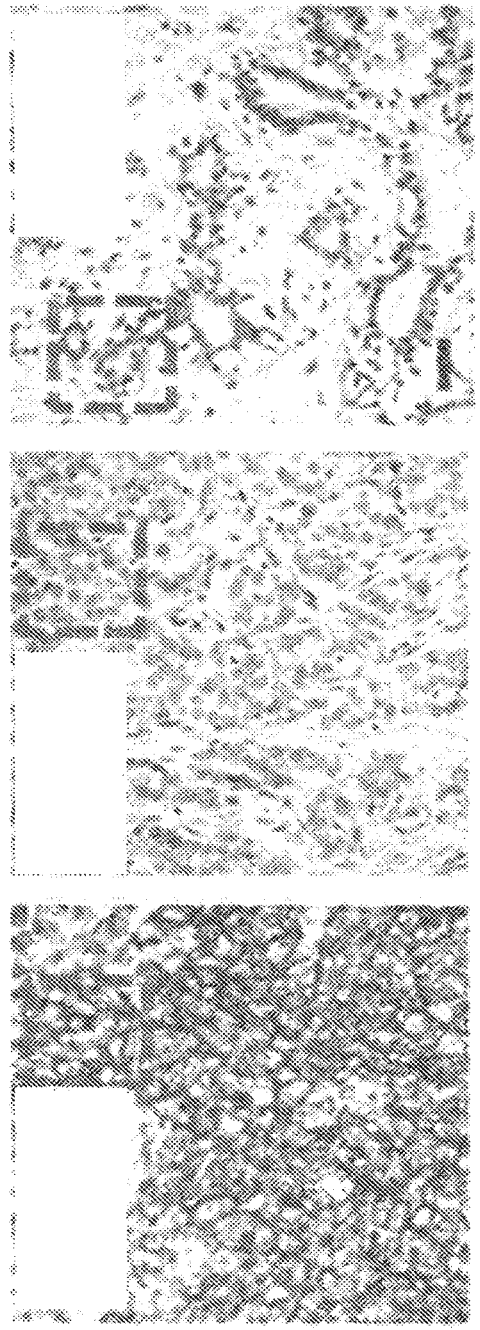
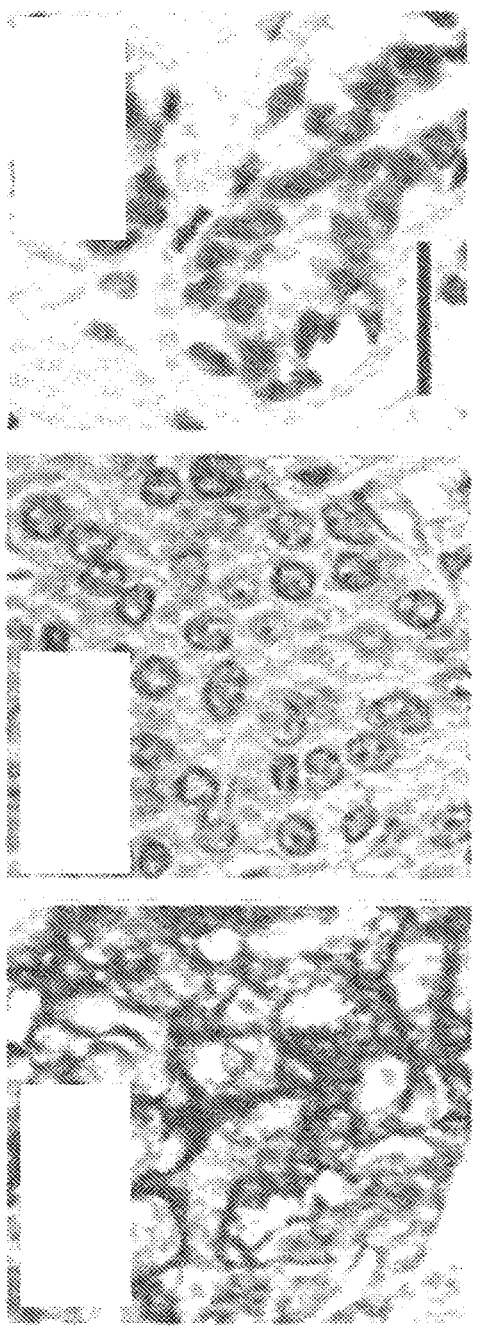

| | Cell Line | ER | PR | HER2 | Invasiveness | Ethnicity | Age | BRCA1 Mutation Status | ICAM1 (Molecules/Cell) | HER2 (Molecules/Cell) |
|---|---|---|---|---|---|---|---|---|---|---|
| TNBC | MDA-MB-231 | - | - | - | High | Caucasian | 51 | Wild Type | 2,250,000±25,000 | 27,500±800 |
| TNBC | MDA-MB-436 | - | - | - | Medium | Caucasian | 43 | Mutant | 756,000±7,600 | 27,000±2,000 |
| TNBC | MDA-MB-157 | - | - | - | Medium | African American | 44 | Wild Type | 751,000±4,400 | 12,500±500 |
| Non-TNBC | MCF7 | + | + | - | Low | Caucasian | 69 | Wild Type | 323,000±900 | 68,000±660 |
| Non-TNBC | HCC1500 | + | + | - | High | African American | 32 | Wild Type | 93,000±550 | 231,000±2,500 |
| Non-TNBC | MDA-MB-361 | + | - | + | Low | Caucasian | 40 | Wild Type | 111,000±1,000 | 875,000±17,000 |
| Non-TNBC | SKBR3 | - | - | + | Low | Caucasian | 43 | Wild Type | 22,900±670 | 5,020,000±12,000 |
| Normal | AG 11143 | - | - | - | Low | African American | 16 | NA | 17,000±2000 | 99,000±1,400 |
| Normal | MCF10A | - | - | - | Low | Caucasian | 36 | Wild Type | 93,000±2,300 | 37,000±3,800 |

FIG. 2A

| | Size (DLS, nm) | Polydispersity Index (PDI) | Zeta-Potential (mV) | Antibody Density (Molecules/µm²) |
|---|---|---|---|---|
| IGG-IONP | 34.7±5.5 | 0.289 | -36.3±1.4 | 4,112±135 |
| HER2-IONP | 36.7±6.0 | 0.267 | -38.5±3.0 | 4,261±61 |
| ICAM-IONP | 36.6±5.6 | 0.272 | -41.4±3.2 | 4,293±93 |

FIG. 2B

METHOD FOR DETECTING OR TREATING TRIPLE NEGATIVE BREAST CANCER

CROSS-REFERENCE TO RELATED APPLICATIONS

This application is a continuation of U.S. Application Ser. No. 15/127,240, filed Sep. 19, 2016, which is a national stage filing under 35 U.S.C. § 371 of International Application No. PCT/US2015/023078, filed Mar. 27, 2015, which claims priority to and is a non-provisional of U.S. provisional patent application Ser. No. 61/970,943 (filed Mar. 27, 2014), the entirety of which are hereby incorporated by reference.

FEDERALLY SPONSORED RESEARCH

This invention was made with government support under Grant Number CA174495, awarded by the National Institutes of Health The Government has certain rights in the invention.

BACKGROUND OF THE INVENTION

The subject matter disclosed herein relates to methods to detecting or treating triple negative breast cancer. Triple negative breast cancers (TNBCs) have high mortality owing to aggressive proliferation and metastasis and a lack of diversified treatment options. TNBCs, which represent 15 to 20 percent of breast cancers, occur more frequently in young women, African American women, and individuals carrying the BRCA1 gene. Currently, there is no curative treatment for TNBC, and the available chemotherapy is associated with significant toxicity and development of drug resistance. As a result, the prognosis for TNBC patients remains poor. The five-year survival rate is less than 74.5% in comparison with 87% for HER2 positive breast cancer and over 90% for ER positive breast cancer. Thus, there is an urgent and unmet need for the development of TNBC targeted therapeutics.

The discussion above is merely provided for general background information and is not intended to be used as an aid in determining the scope of the claimed subject matter.

BRIEF DESCRIPTION OF THE INVENTION

A method of detecting triple negative breast cancer (TNBC) is provided. Overexpression of ICAM-1 is linked to an increased risk of TNBC. A composition of matter is also provided that binds an anti-ICAM-1 antibody to a nanoparticle. The composition may be used as an imaging agent and/or a therapeutic targeting agent. A therapeutically active molecule may be bound to the composition to provide targeted therapy.

In a first embodiment, a method of detecting a high risk of triple negative breast cancer (TNBC) is provided. The method comprises steps of quantifying an expression level of intercellular adhesion molecule-1 (ICAM-1) in a sample of human breast tissue; comparing the expression level to a predetermined standard level of ICAM-1 expression; and determining the human breast tissue has a high risk of triple negative breast cancer by finding the expression level is greater than the predetermined standard level of ICAM-1 expression.

In a second embodiment, a method of localizing a nanoparticle proximate triple negative breast cancer cells is provided. The method comprises steps of introducing a probe into a human breast tissue, the probe comprising an anti-ICAM-1 antibody bound to a nanoparticle; permitting the anti-ICAM-1 antibody to preferentially locate at triple negative breast cancer tissue in the human breast tissue.

In a third embodiment, a composition of matter is provided comprising a nanoparticle bound to an anti-ICAM-4 antibody.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1B is a depiction of human triple negative breast cell (TNBC) tissue;

FIG. 1C is a depiction f human non-TNBC tissues (ER+/PR+/HER2−);

FIG. 1D depicts normal breast epithelium stained with an anti-human ICAM-1 antibody;

FIG. 1E is a depiction of human triple negative breast cell (TNBC) tissue;

FIG. 1F is a depiction of human non-TNBC tissues (ER+/PR+/HER2−);

FIG. 1G depicts normal breast epithelium stained with an anti-human ICAM-1 antibody;

FIG. 2A is a table showing human TNBC, non-TNBC, and normal cell lines with their ICAM-1 and HER2 surface protein densities measured by FACS.

FIG. 2B is a table showing the characterization of as-synthesized IGIO, HEIO, and ICIO;

FIG. 38 is a transmission electron microscopy of the magnetic iron oxide nanoparticles;

DETAILED DESCRIPTION OF THE INVENTION

Figure 1A:
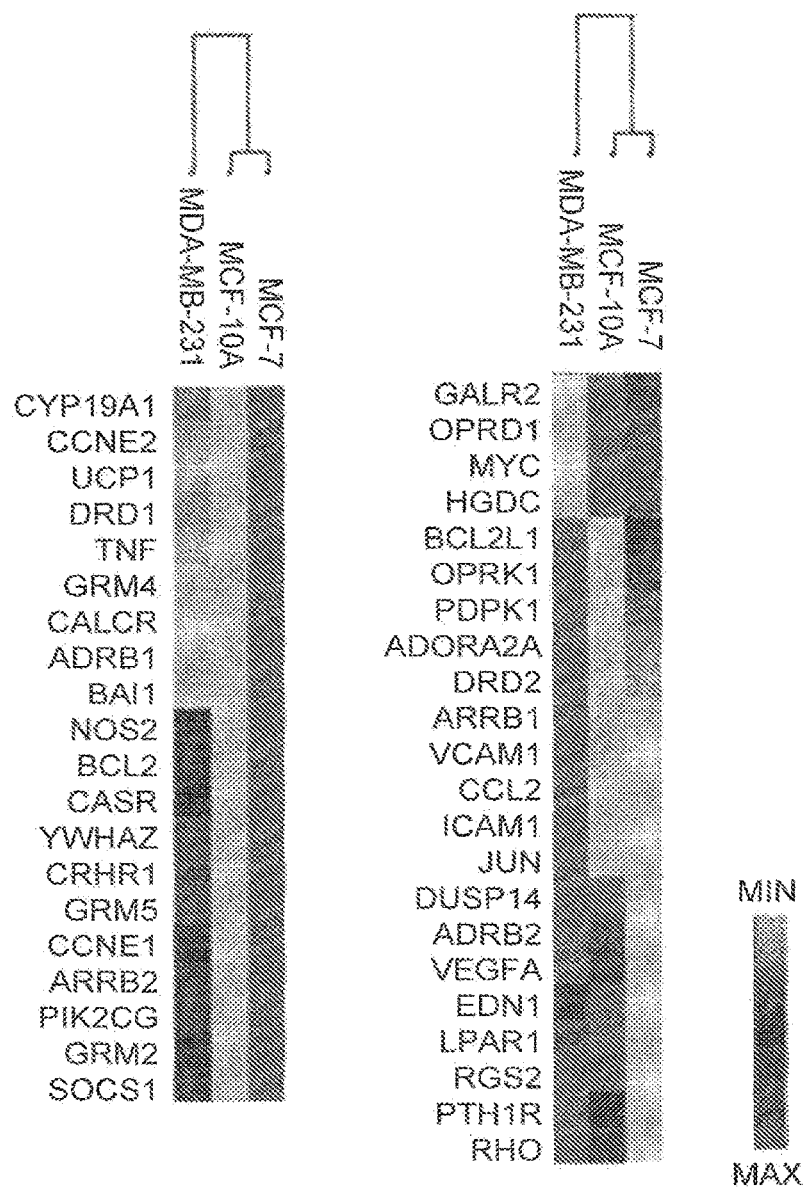
FIG. 1A is gene expression analysis for eighty-four G-protein-coupled receptor (GPCR) signaling genes.

This disclosure pertains to methods for detecting triple negative breast cancer (TNBC) utilizing intercellular adhesion molecule-1 (ICAM-1) as a target and biomarker, ICAM-1 serves as a TNBC therapeutic target that enables development of multiple types of TNBC-targeted treatments based on the high affinity ICAM-1 ligands (natural and designed) or antibodies targeting with TNBC tumors, including monoclonal antibodies, antibody-drug conjugates, liposomes and nanoparticles. The disclosed methods may be applied in TNBC-targeted treatments based on the overexpression of ICAM-1 in TNBC tissues and cells and the ICAM-1's function in TNBC metastasis, which is involved with cell apoptosis. This disclosure also pertains to the overexpression of intercellular adhesion molecule-1 (ICAM-1, CD54) in human TNBC cell lines and tissues, and demonstrates that ICAM-1 is an effective TNBC biomarker for TNBC-targeted diagnosis and therapy.

Triple negative breast cancers (TNBCs) have high mortality owing to aggressive proliferation and metastasis and a lack of effective therapeutic options. TNBCs, which represent 15 to 20 percent of all breast cancers, occur more frequently in women under 50 years of age, African American women, and individuals carrying the breast cancer, early onset 1 (BRCA1) gene. TNBCs comprise a heterogeneous group of tumors with diverse histology and genetic make-up that share the common feature of low expression of the estrogen receptor (ER), progesterone receptor (PR), and human epidermal growth factor receptor 2 (HER2). TNBC patients therefore do not benefit from hormone or HER2 targeted therapies, leaving chemotherapy as a limited treatment option. As a result, the prognosis for TNBC patients remains poor. The 5-year survival rate of patients with TNBC is less than 74.5% in comparison with 87% for patients with HER2 positive breast cancer and over 90% for patients with ER positive breast cancer. While a novel targeted therapy using the overexpression of a specific cancer cell membrane molecule can facilitate the spatial and temporal delivery of therapeutics, there is yet no available therapeutic that can discriminate between TNBC cells and non-neoplastic cells.

ICAM-1 antibody conjugated iron oxide nanoparticles (ICAM-IOs) were synthesized as a magnetic resonance imaging (MRI) probe to evaluate tumor targeting. Quantitative analysis of TNBC cell surface expression predicted ICAM-IOs' targeting capability. The ICAM-IOs demonstrated significant targeting potential performing equal or better than human epidermal growth factor receptor-2 (HER2) antibody conjugated iron oxide nanoparticles (HER2-IOs) targeted to HER2 overexpressing cell lines.

To identify a TNBC target, screening was performed of G-protein-coupled receptor (GPCR) signaling proteins—the largest family of cell-surface molecules involved in signal transmission. GPCRs are overexpressed in breast cancer. Malignant cells can usurp the functions of GPCRS to survive and proliferate, elude the immune system, expand the blood supply, colonize tissues, and spread to other organs, making them potential candidates as therapeutic and diagnostic targets for TNBC.

A real-time PCR array was used to obtain the expression profile of 84 genes involved in GPCR-mediated signal transduction pathways, including bioactive lipid receptors, metabotropic glutamate receptors, and proteins in the calcium signaling pathway, in three cell lines: MDA-MB-231 (TNBC), MCF7 (non-TNBC, ER+/PR−/HER2−), and MCF10A (a nonneoplastic, human mammary epithelial cell line) (as shown in Table 2).

FIG. 1A demonstrates a collection of 42 differentially expressed genes in MDA-MB-231 cells compared with MCF7 and MCF10A. The candidates were narrowed down to four genes: ICAM-1 (CD54), lysophosphatidic acid receptor 1 (LPAR1), Chemokine (C-C motif) ligand 2 (CCL2), and vascular cell adhesion molecule 1 (VCAM-1) based on their up-regulated levels relative to MCF7 and MCF10A cells and expression on cell membranes. LPAR1 and CCL2 are expressed in multiple cell types. LPAR1 exhibits high expression in smooth muscle cells, platelets, the spinal cord, and the hypothalamus. CCL2 is anchored on endothelial cells and is secreted by monocytes, macrophages, dendritic cells and osteoblasts. ICAM-1 and VCAM-1 are well-recognized biomarkers for inflammation. Unlike VCAM-1, ICAM-1 is expressed at low levels in normal tissues except the tonsil, adrenal gland, and spleen. ICAM-1 is present on endothelial cells at levels lower than TNBC cells (Table 1), Due to its specificity, ICAM-1 was chosen for further evaluation as a TNBC target. While the overexpression of ICAM-1 was not solely determinate of TNBC the high degree of correlation demonstrates overexpression of ICAM-1 is strongly linked to an increased risk of TNBC.

TABLE 1

ICAM-1 expression on HUVEC is experimentally lower than TNBC cells by flow cytometry measurement.

| | ICAM-1 (molecules/cell) |
|---|---|
| MDA-MB-231 | 2,350,000 ± 25,000 |
| MDA-MB-157 | 751,000 ± 4400 |
| MDA-MB-436 | 756,000 ± 7,600 |
| HUVEC | 284,000 ± 4,600 |
| MCF10A | 93,000 ± 2,300 |

As shown in FIGS. 1B to 1G, to validate that ICAM-1 is highly overexpressed in TNBC tumors, immunohistochemistry (IHC) was applied to 149 human breast tumor tissues representing different ER/PR/HER2 status. FIG. 1B and FIG. 1E depict human TNBC tissues. FIG. 1D and FIG. 1G are normal breast epithelium stained with an anti-human ICAM-1 antibody. FIG. 1C and FIG. 1F are non-TNBC tissues (ER+/PR+/HER2−). ICAM-1 staining in TNBC tissues was stronger and in more cells (FIG. 1B and FIG. 1D) compared to non-TNBC tissues (FIG. 1C and FIG. F) and normal epithelium (FIGS. 1D and G).

Figure 1H:
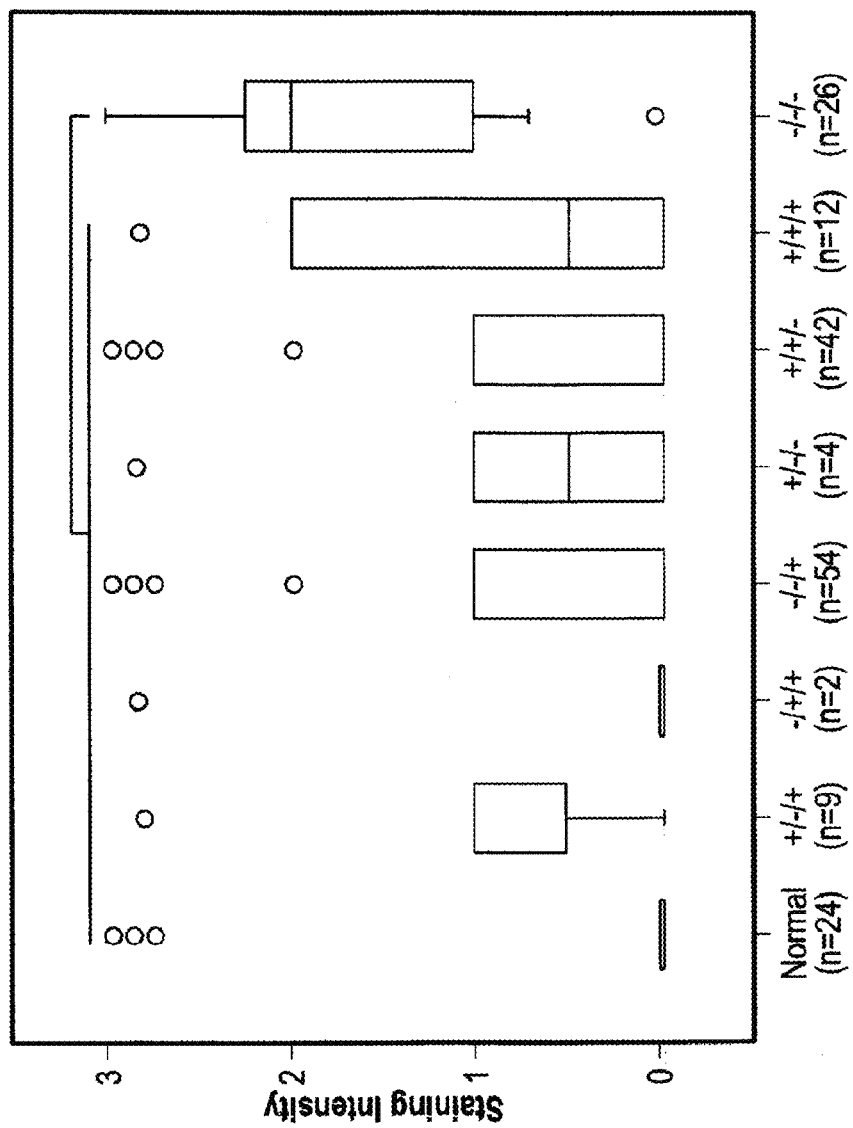
FIG. 1H is a graphic quantification of ICAM-1 staining intensities in different subtypes of breast cancers.

FIG. 1H is a graphic quantification of ICAM-1 staining intensities in different subtypes of breast cancers (status of ER/PR/HER2: +/−/+; −/+/+; −/−/+; +/−/−; +/+/−; +/+/+; and −/−/− (TNBC)) and normal breast tissue. Data are presented as a box-and-whisker plot. * P<0.05;  P<0.001; * P<0.0001 compared with TNBC tissues. TNBC exhibited a significant increase in ICAM-1 expression compared to various other subtypes of breast cancer and normal epithelium. The finding that ICAM-1 is overexpressed in 26 human TNBC tissues provided clinical evidence supporting ICAM-1 as a potential target for TNBC.

Figure 1I:
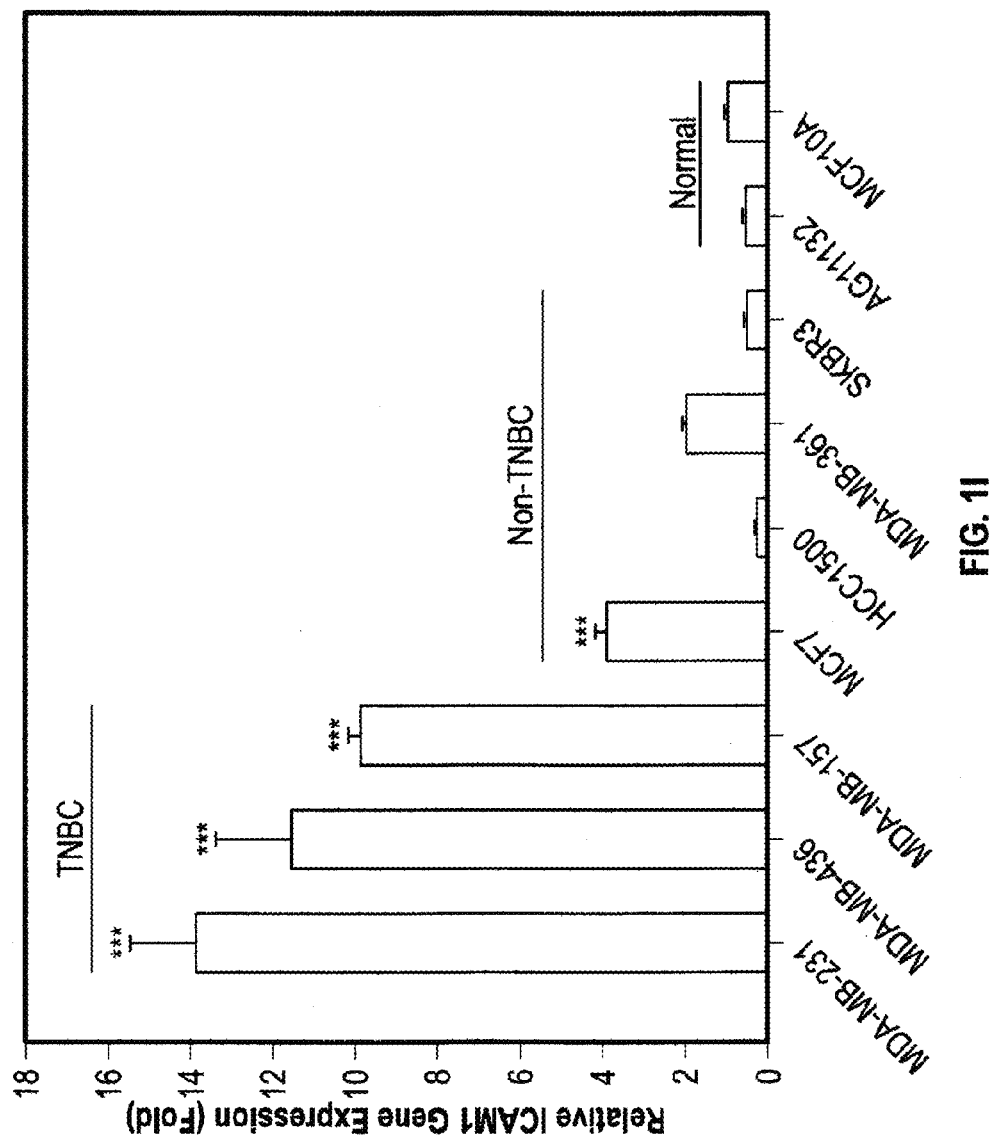
FIG. 1I graphically depicts relative ICAM-1 gene expression in TN BC and non-TNBC cells.

Because TNBCs are more prevalent in women under 50 years of age, African-American women, and individuals carrying the BRCA1 gene mutation. ICAM-1 levels were analyzed in seven breast cancer cell lines—derived from patients of African American and Caucasian origin, age spanning from 32 to 69 years, and wild type and mutant BRCA1 gene status—relative to non-neoplastic, human mammary epithelial cells MCF10A and AG1132. As shown in FIG. 1I, TNBC cells: MDA-MB-231, MDA-MB-436, and MDA-MB-157 exhibited 13.9, 11.6, and 9.9-fold higher ICAM-1 gene expression than MCF10A, respectively (even higher fold relative to AG1132). In non-TNBC cells, MCF7 and MDA-MB-361 showed elevated ICAM-1 gene expression relative to non-neoplastic cells, but at markedly lower levels than TNBC cells. ICAM-1 fold change is relative to GAPDH (* P<0.001). (J-R) are representative fluorescence microscope images of ICAM-1 immunofluorescent staining in MDA-MB-231.

Consistent with ICAM-1 gene expression levels, TNBC cells exhibited between 8 and 25-fold higher ICAM-1 surface protein levels than non-TNBCs and normal cells (FIG. 2A). When compared to the surface protein density of HER2, a clinical biomarker for breast cancer, the ICAM-1 surface protein density (751.000-2,350,000 molecules/cell) on TNBC cells was comparable to the HER2 surface density (875,000-5,020,000 molecules/cell) measured on HER2 positive breast cancer cells (MDA-MB-361 and SKBR3). Immunofluorescent staining of ICAM-1 overexpression in TNBC cells revealed greater ICAM-1 surface staining on TNBCs relative to non-TNBCs and non-neoplastic cells. Furthermore, ICAM-1 was largely localized on the TNBC cell membranes, suggesting it could be recognized and bound by targeted therapeutic agents. Based on the above results, ICAM-1 expression is not ubiquitous in all breast cancers. ICAM-1 is overexpressed on the surface of TNBC cells, and thus can be used as a biomarker for TNBC-targeted therapy.

Figure 3A:
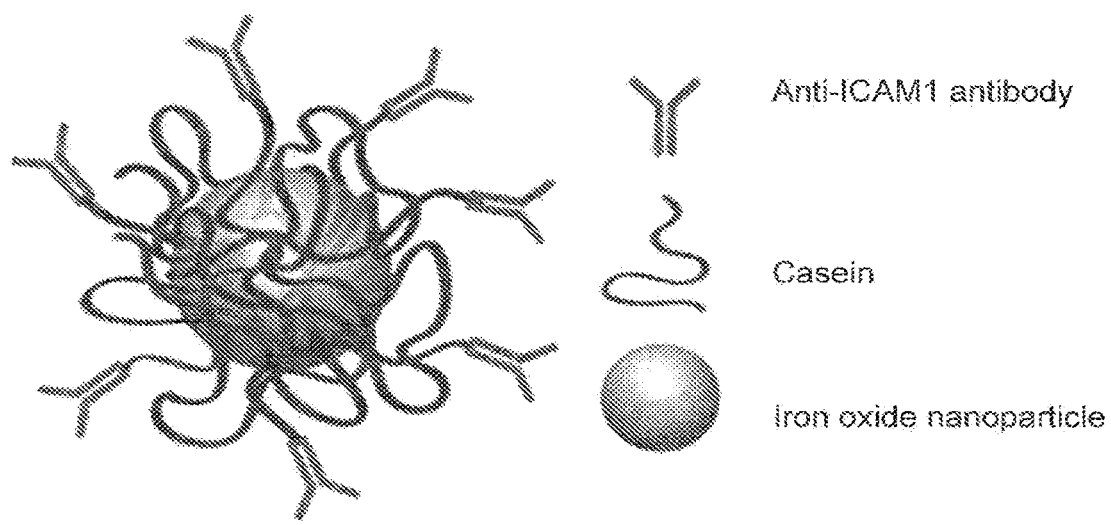
FIG. 3A is a schematic depiction of a magnetic iron oxide (IOs) nanoparticle conjugated with ICAM-1 antibodies (ICAM-IOs)
Figure 3B:
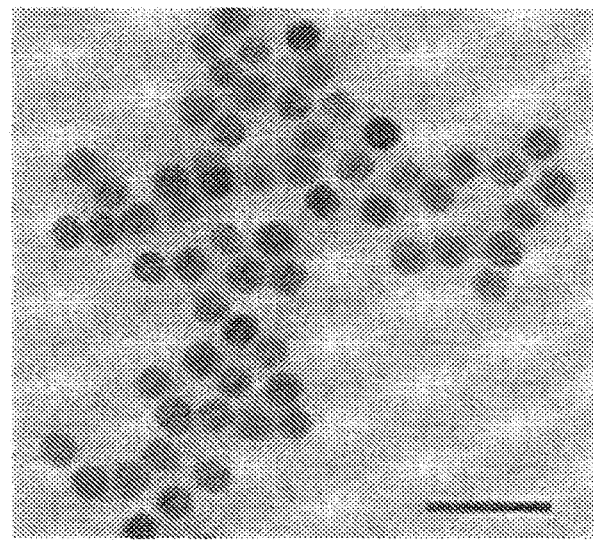
FIG. 3C is a graph depicting the relative binding of magnetic iron oxide nanoparticles to various cell lines.

As shown in FIG. 3A, to test ICAM-1 targeting for TNBC, a TNBC-targeting magnetic resonance imaging (MRI) probe was synthesized using magnetic iron oxide (IOs) nanoparticles conjugated with ICAM-1 antibodies (ICAM-IOs). ICAM-1 antibodies are covalently conjugated to casein coated IOs via EDC/NHS chemistry. Similarly, casein coated IOs were conjugated with Herceptin (humanized anti-HER2 antibody) (IHER2-IO) or non-specific IgG (IGG-IOs) as controls for non-targeted delivery. The morphology and monodispersity of ICAM-IOs were examined by transmission electron microscopy (TEM, FIG. 3B) and dynamic light scattering (DLS). ICAM-IOs, with a core diameter of 15 nm, had a mean hydrodynamic radius of 36.6±5.6 nm and a zeta potential of −41.4±3.2 mV. The antibody density for ICAM-IO, IGG-IO, and HER2-IO was determined experimentally using FITC-labeled antibodies (FIG. 2B). Approximately two or three antibody molecules were conjugated to each particle.

Figure 3C:
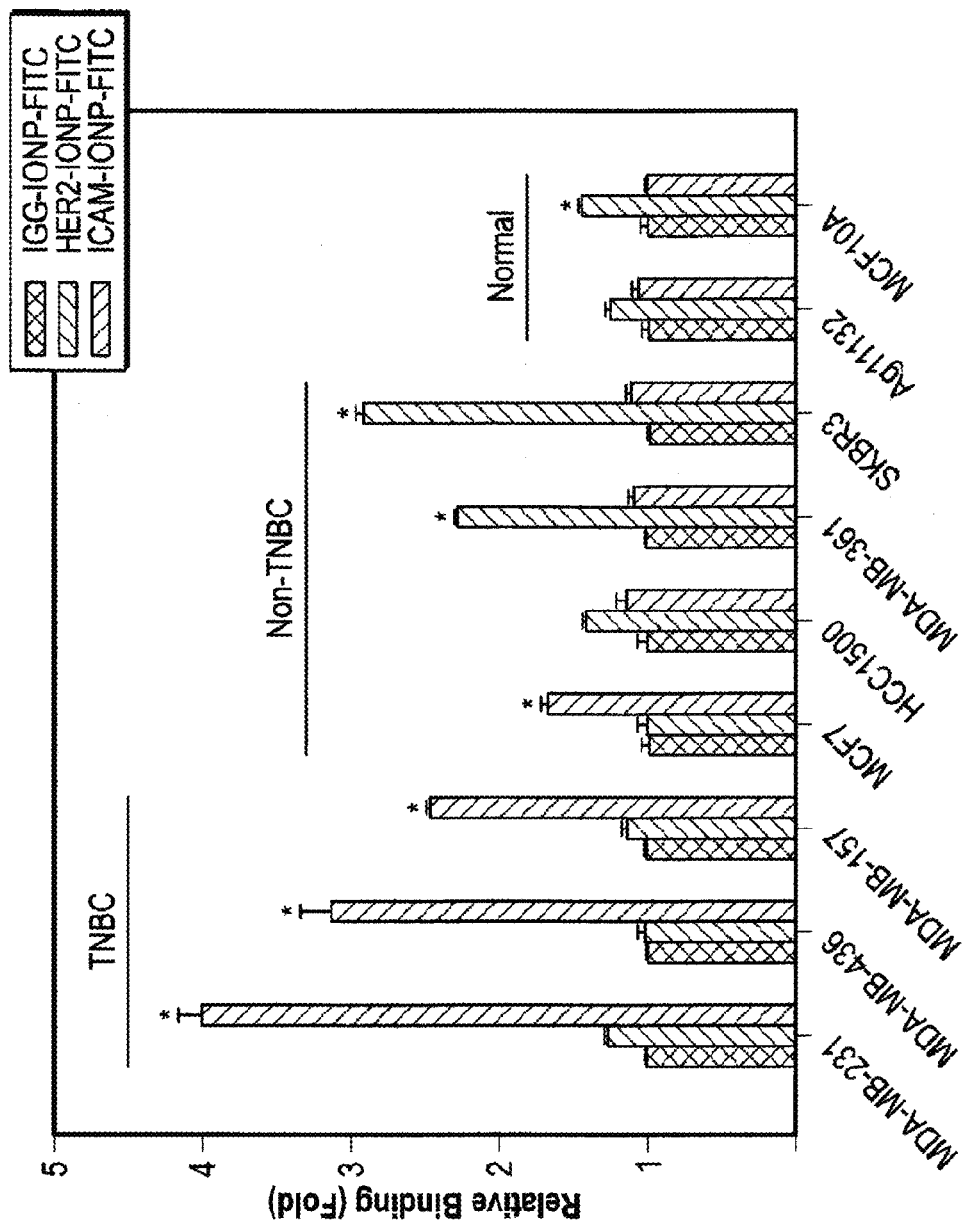

Effective targeting of TNBC cells via the ICAM-1 antibody was first evaluated in vitro by the binding and uptake of FITC-labeled ICAM-IOs, IGG-IOs, and HER2-IOs. Normalized fluorescence intensity data demonstrated that TNBC cells exhibited 2.4 to 4-fold greater binding to ICAM-IOs than IGG-IOs or HER2-IOs due to the abundance of ICAM-1 expression (FIG. 3C). Quantitative analysis of ICAM-1 surface protein expression directly correlated with increased binding of ICAM-IOs. In comparison, HER2-IOs showed positive targeting to HER2 positive cells but failed to target TNBCs due to their HER2 deficiency. Using a Prussian blue staining assay to examine the presence of iron oxide, the strong and specific binding of ICAM-IOs to TNBC cells was confirmed compared to minimal binding to non-TNBC and normal cell lines. Analogous patterns of binding were observed between ICAM-IO and HER2-IO to both ICAM-1 and HER2 overexpressing cell lines, respectively. These results indicate that ICAM-IOs exhibit ICAM-1 targeting activity and specificity.

Figure 4A:
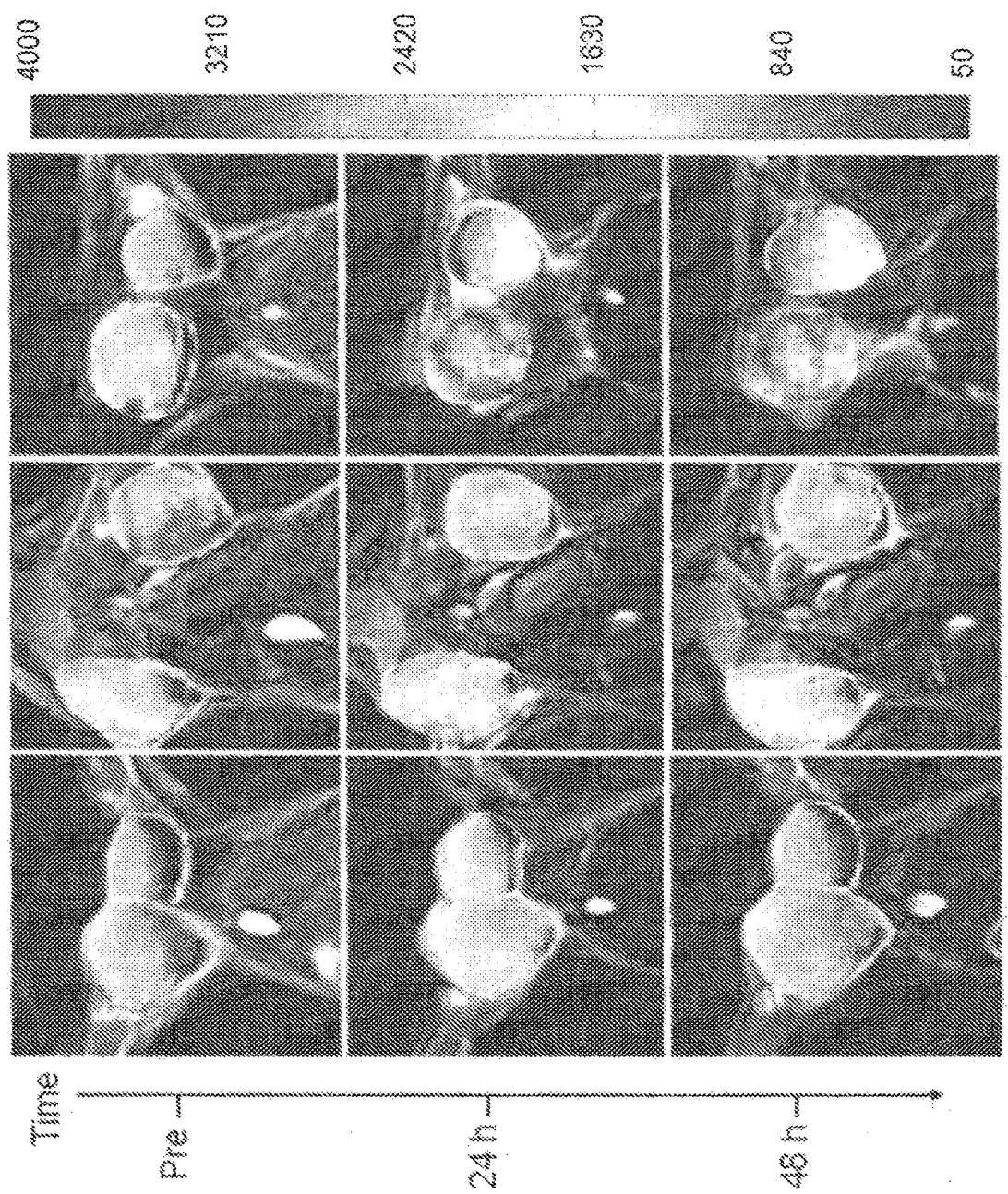
FIG. 4A depicts magnetic resonance (MR) images of different magnetic iron oxide nanoparticles that bind to IGG, HER2, or ICAM-1, respectively.
Figure 4B:
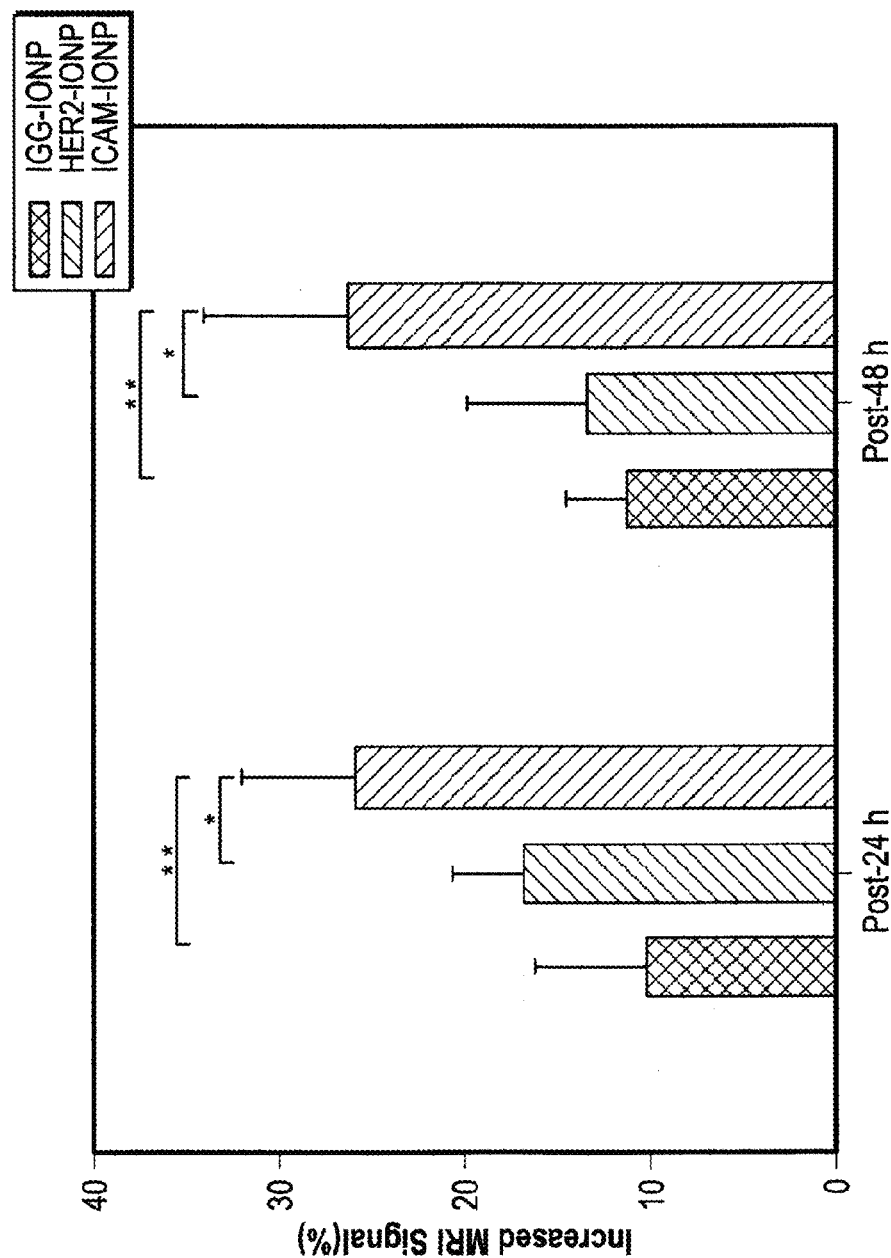
FIG. 4B is a graph quantifying the increased MR signal resulting from the contrast provided by the respective magnetic iron oxide nanoparticles.

The ability of ICAM-IOs for targeted imaging of T NBC tumors in vivo were examined by MR imaging using a xenograft TNBC mouse model. MDA-MB-231 cells were subcutaneously implanted in immunodeficient nude mice. MRI was performed on three groups of tumor bearing mice intravenously injected with IGG-IO, HER2-IO, or ICAM-IO when tumors reached 1 cm³ in volume. Each group was scanned at pre-injection and 24 h and 48 h post-injection with a set of MRI sequences, including $T_1$, $T_2$-weighted spin echo imaging, and $T_2$ relaxometry. $T_2$ weighted MR images presented in FIG. 4A show decreased signals in the regions of the tumor as the result of enhanced $T_2$ contrast from uptake of IO probes in tumors. Quantification of MRI signals in three groups demonstrated a 10% (IGG-IO), 17% (HER2-IO), and 26% (ICAM-IO) signal drop at 24 h after administration of the probes, which lasted at least 48 h (FIG. 4B). ICAM-IOs significantly improved MRI contrast by actively targeting the TNBC tumor via ICAM-1 binding. It is worth noting that HER2-targeting MRI probes were reported to change the MRI signal by 18 to 46% in HER2 positive breast tumors, comparable to the ICAM-1 targeting MRI probe demonstrated in TNBC tumors in the current study.

Figure 4C:
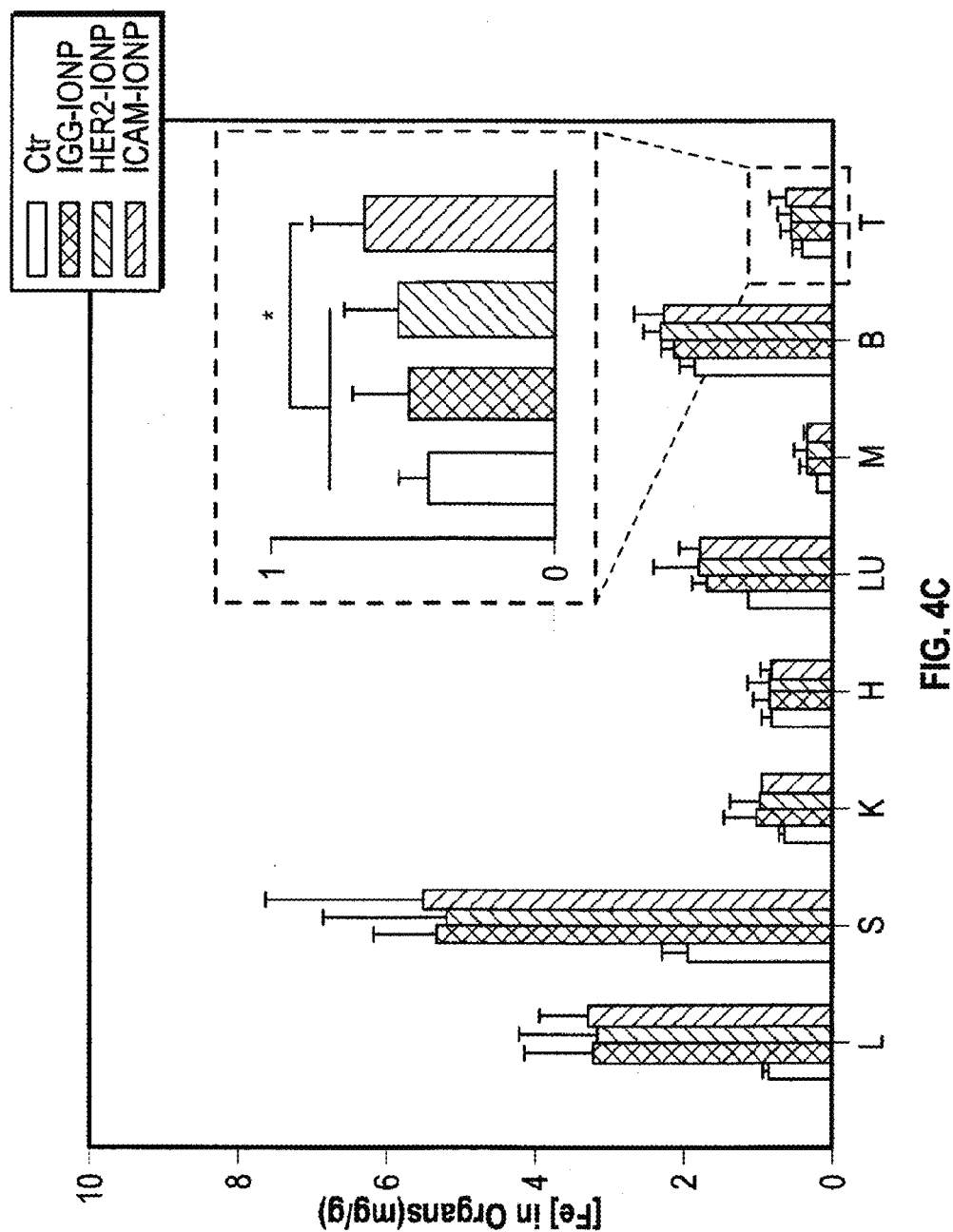
FIG. 4C shows comparative iron accumulation in seven organs harvested from mice at 48 h after a single tail vein administration of IGG-IOs, HER2-IOs, and ICAM-IOs.
Figure 5A:
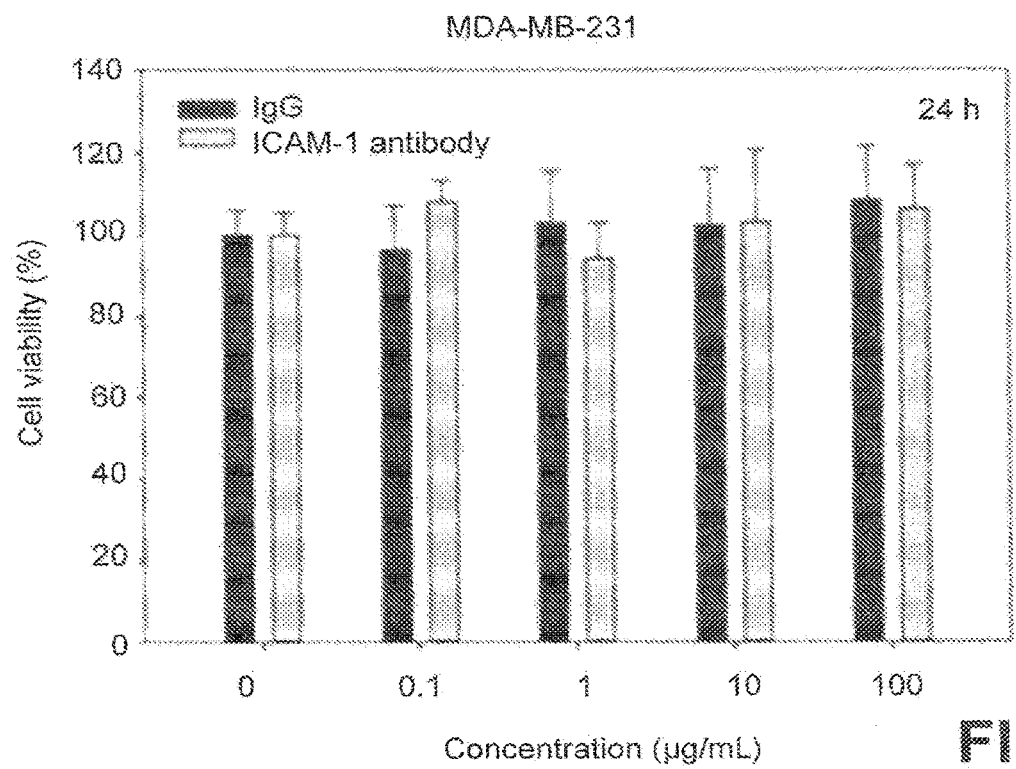
FIG. 5A graphically depicts cell viability as a function of IgG and ICAM-1 antibody concentration after twenty-four hours for MDA-MB-231 cell lines.
Figure 5B:
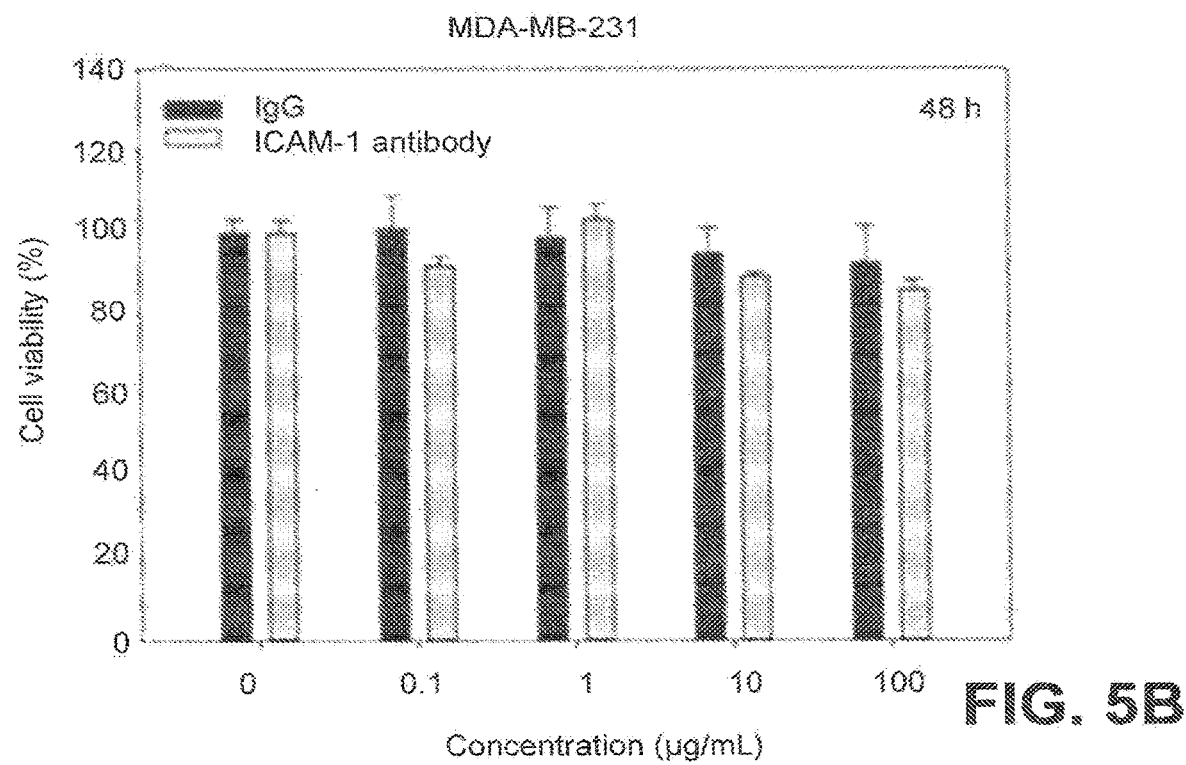
FIG. 5B graphically depicts cell viability as a function of IgG and ICAM-1 antibody concentration after forty-eight hours for MDA-MB-231 cell lines.
Figure 5C:
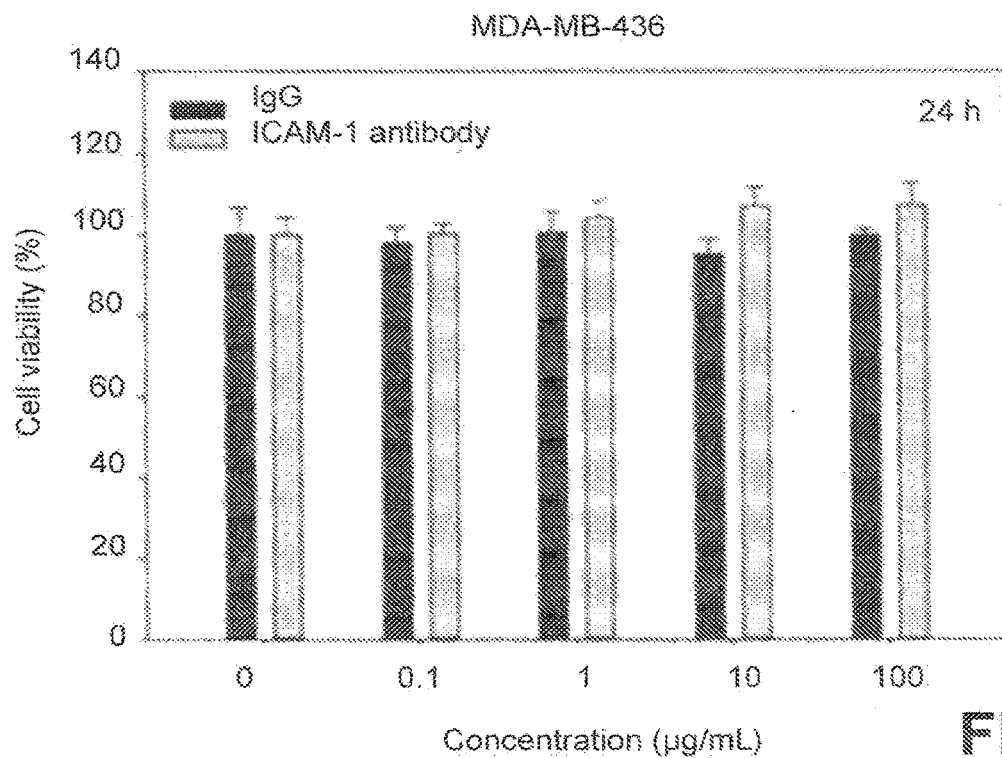
FIG. 5C graphically depicts cell viability as a function of IgG and ICAM-1 antibody concentration after twenty-four hours for MDA-MB-436 cell lines.
Figure 5D:
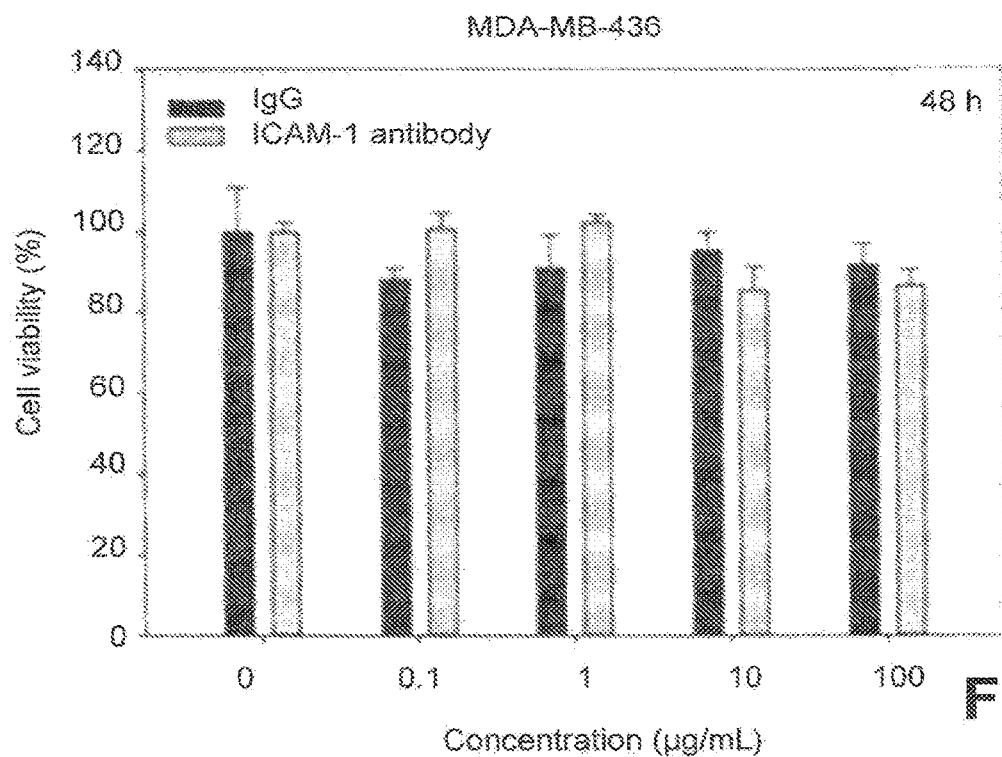
FIG. 5D graphically depicts cell viability as a function of IgG and ICAM-1 antibody concentration after forty-eight hours for MDA-MB-436 cell lines.
Figure 5E:
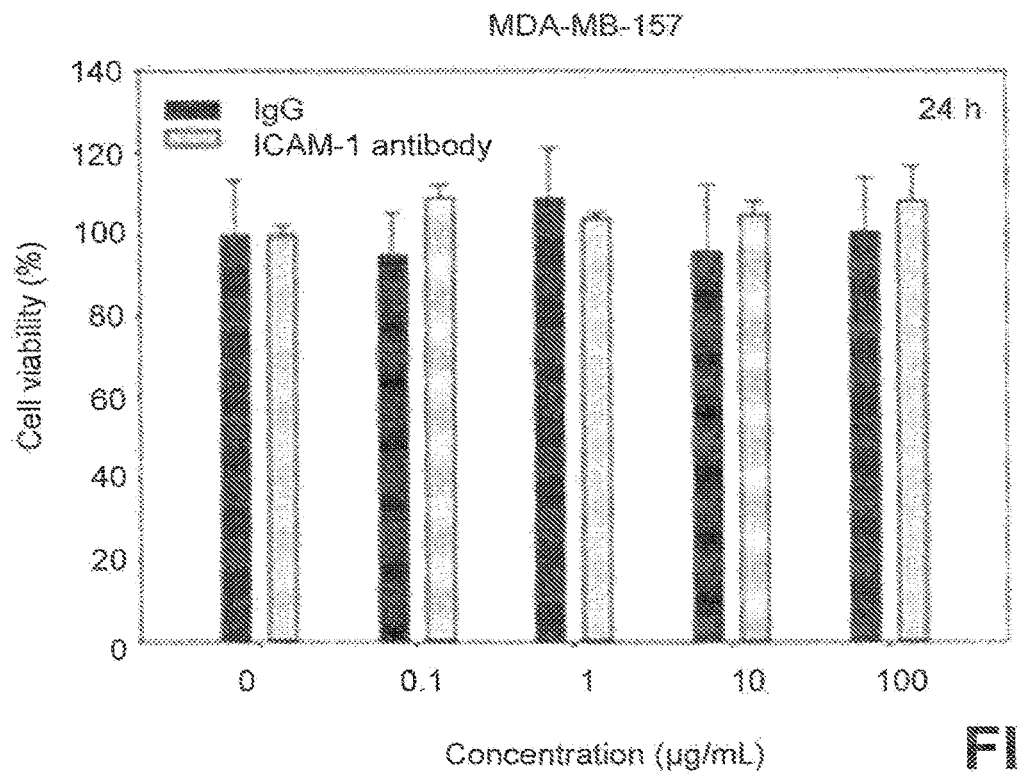
FIG. 5E graphically depicts cell viability as a function of IgG and ICAM-1 antibody concentration after twenty-four hours for MDA-MB-157 cell lines.
Figure 5F:
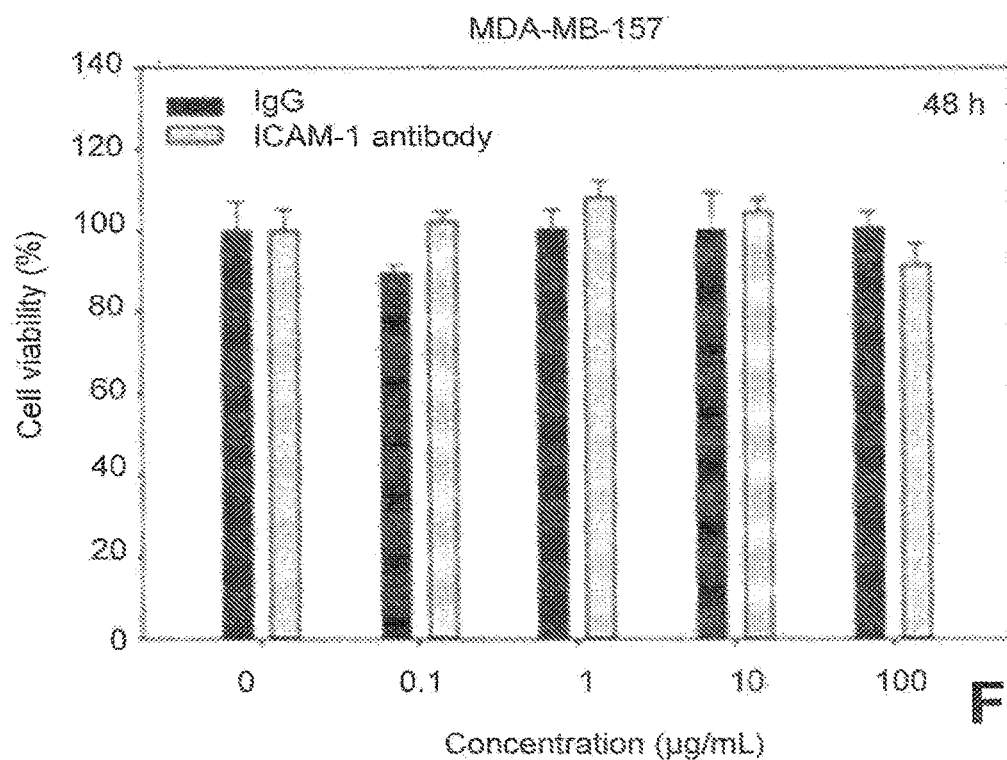
FIG. 5F graphically depicts cell viability as a function of IgG and ICAM-1 antibody concentration after forty-eight hours for MDA-MB-157 cell lines.
Figure 6A:
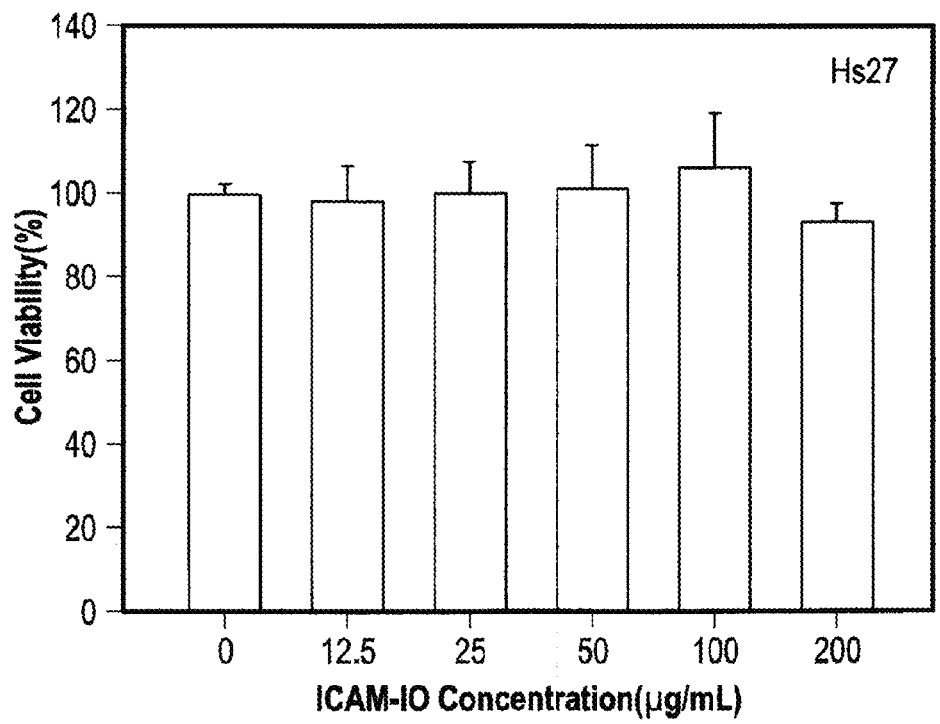
FIG. 6A graphically depicts cytotoxicity effects of ICAM-IO in HS27 (human fibroblast) as a function of ICAM-IO concentration.
Figure 6B:
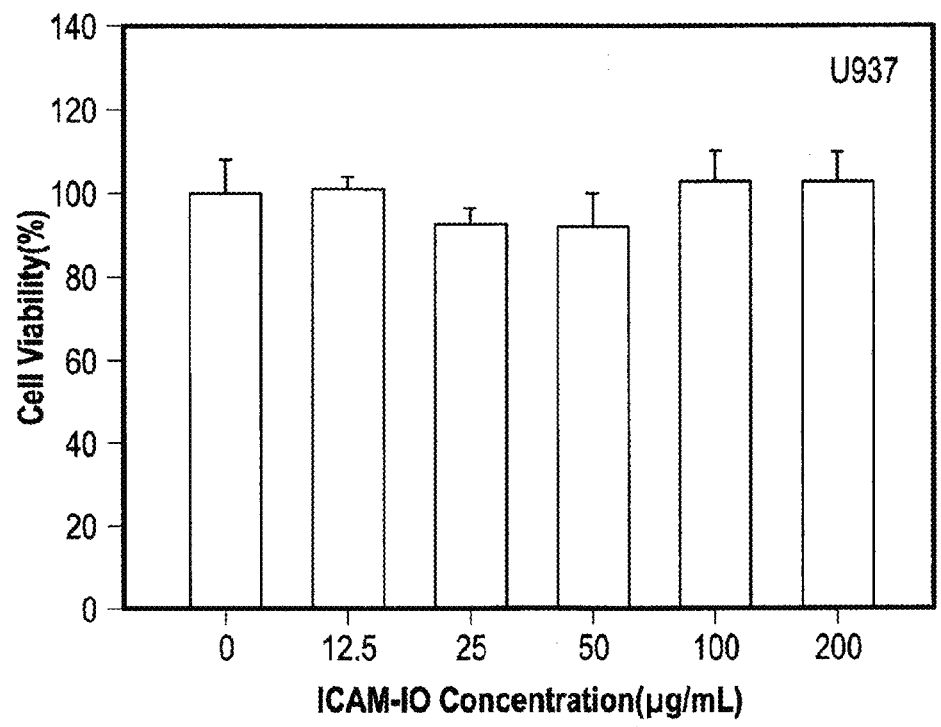
FIG. 6B graphically depicts cytotoxicity effects of U937 (human macrophages) as a function of ICAM-IO concentration.
Figure 6C:
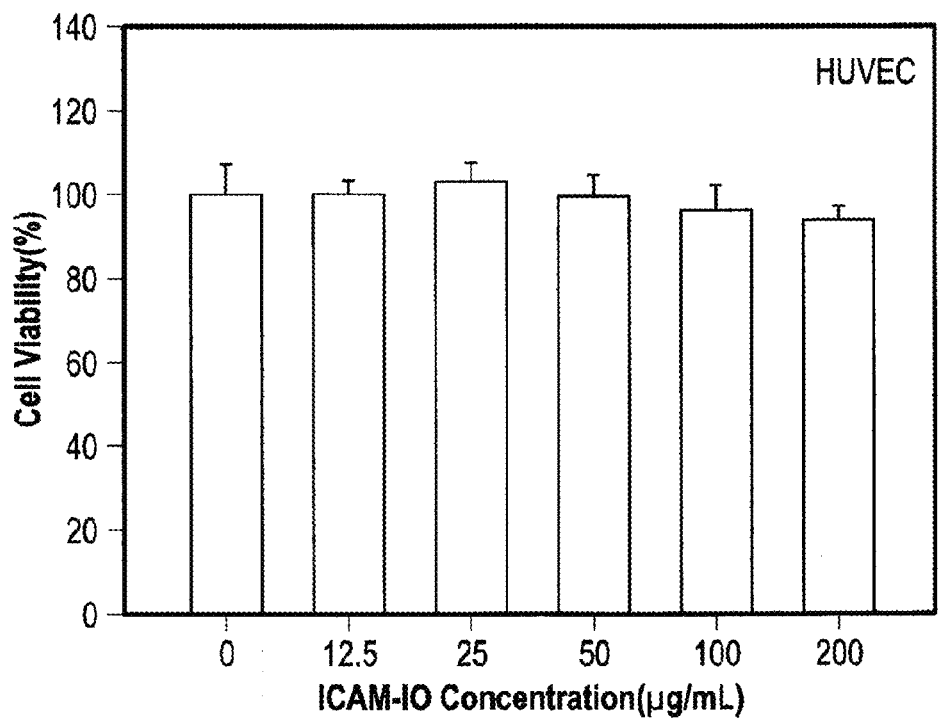
FIG. 6C graphically depicts cytotoxicity effects of HUVEC (Human umbilical endothelial ceils) as a function of ICAM-IO concentration.

The biodistribution and tumor accumulation of MRI probes were evaluated. FIG. 4C shows comparative iron accumulation in seven organs harvested from mice at 48 h after a single tail vein administration of IGG-IOs, HER2IOs, and ICAM-IOs. Correlating with the in vivo MRI results, the iron accumulation of ICAM-IOs in TNBC tumors was 3.7- and 2.1-fold higher than that of IGG-IOs and HER2-IOs with reference to untreated tumors, respectively (FIG. 4C inset). To further confirm the targeting of ICAM-IOs to the tumor, the in vivo MRI results were corroborated with histology. TNBC tumor sections were stained with ICAM-1 antibody, HER2 antibody, hematoxylin and eosin (H&E), and Prussian blue. Consistent with the MRI findings, tumors from mice receiving ICAM-IOs showed a high level of ICAM-1 expression and strong Prussian blue staining of IOs. In contrast, Prussian blue staining was low in tumors receiving IGG-IOs or HER2-IOs. Low HER2 surface expression in TNBC tumors did not result in significant HER2-IO accumulation. Thus, results from the in vivo MRI experiments with ICAM-1 targeting ICAM-IOs suggest that the uptake of ICAM-IOs is driven by ICAM-1 expression on TNBCs.

Figure 7A:
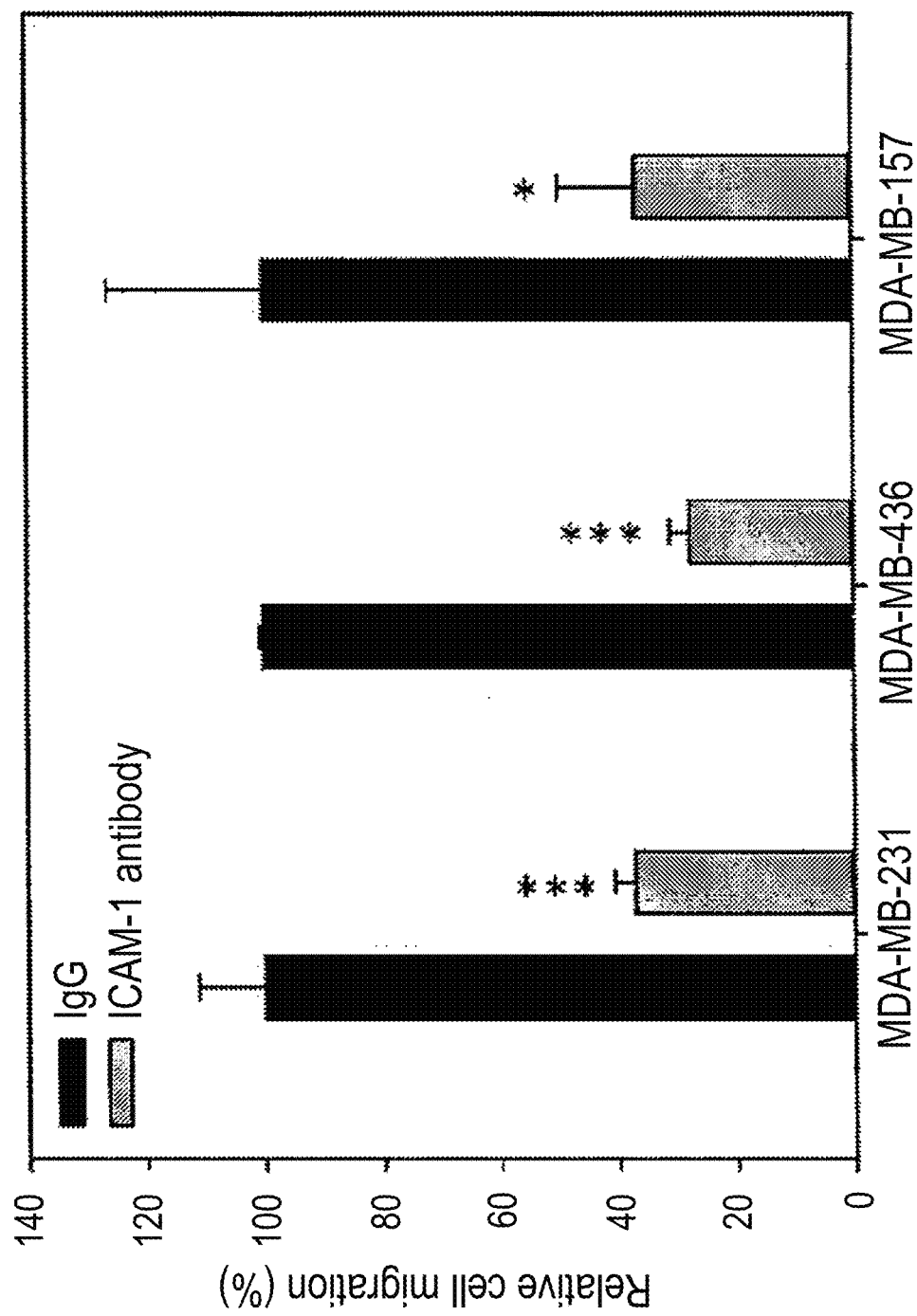
FIG. 7A is a graph shoving a reduction in TNBC cell migration caused by ICAM-1 antibody relative to IgG.
Figure 7B:
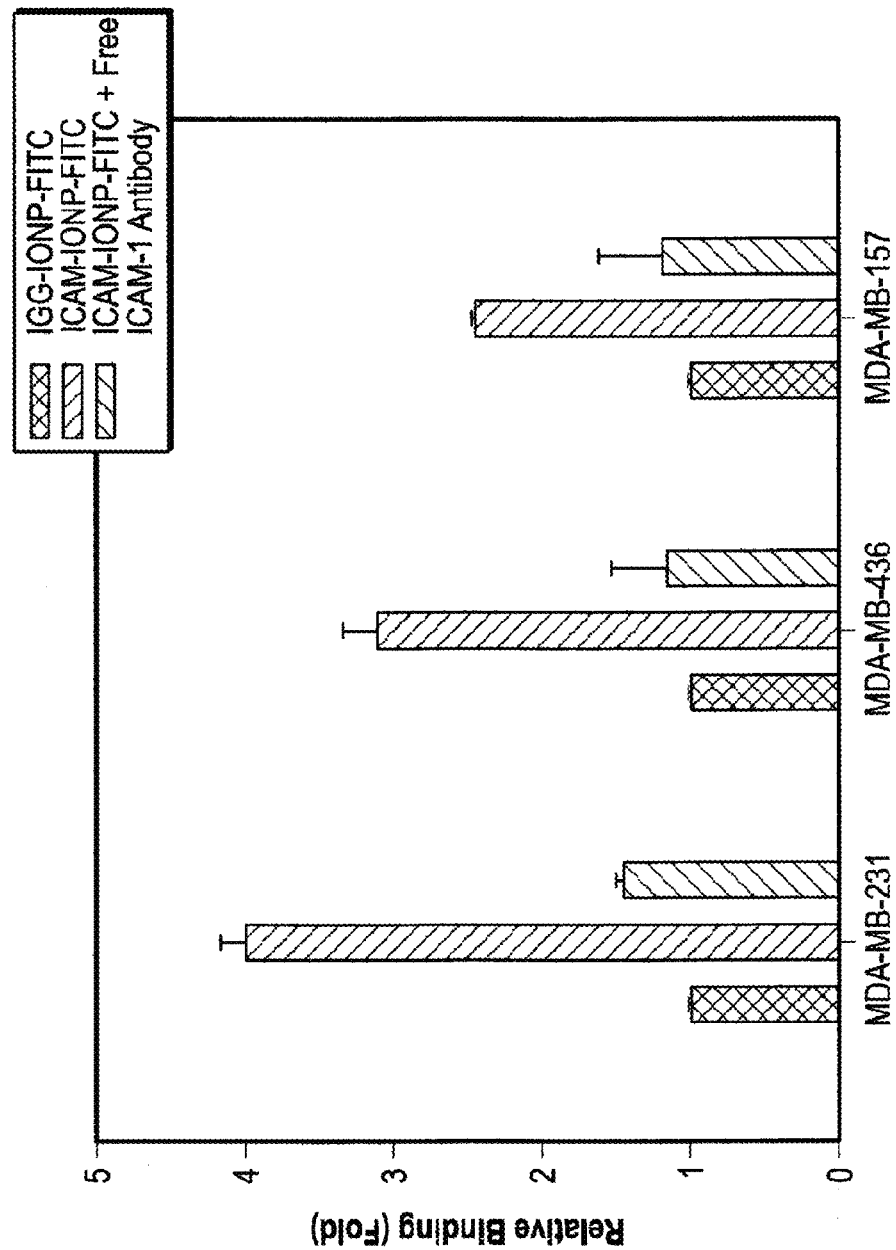
FIG. 7B is a graph showing cellular binding of IgG-IONP, ICAM1-IONP, or ICAM1-IONP with free ICAM1 antibody in three TNBC cell lines.

It is noteworthy that the discovery of ICAM-1 as a TNBC biomarker reveals new functions of this well-characterized receptor, which can be utilized in clinical applications. The discovery that ICAM-1 is a promising TNBC target and biomarker may lead to an effective ICAM-1 targeting strategy for imaging and treatment of TNBC. Previous studies in wound healing, rheumatoid arthritis, and acute stroke demonstrated that enlimomab (anti-ICAM-1 antibody) was well tolerated by different patient groups, indicating that it may be safe and well tolerated in humans. Although in vitro the ICAM-1 antibody did not affect TNBC cell proliferation or cell viability (FIG. 5A to FIG. 5F and FIG. 6A to FIG. 6C), the ICAM-1 antibody was observed to significantly reduced TNBC cell migration (FIG. 7A), ICAM-IOs are biologically nontoxic at test concentration of about 200 μg per mL It is known that an ICAM-1 antibody blockade resulted in ICAM-1 molecules lacking cytoplasmic tails that were not capable of activating Rho proteins. Similar anti-tumor activity of the ICAM-1 antibody or siRNA was observed in several human cancers.

Molecular targeting agents that use ICAM-1 include: nanoparticles, including the aforementioned nanoparticles, small molecular inhibitors, antibodies and antibody fragments, engineered peptides and nucleic acids, antibody drug conjugates, nanoscale drug delivery systems (such as liposomes, polymeric nanoparticles), molecular imaging contrast enhancement reagents (MRI, PET, CT. Ultrasound, fluorescent, and near-infrared imaging contrast enhancement reagents). Examples of suitable molecular inhibitors include ursolic acid; 4-[(4-methylphenyl)thio]thieno[2,3-c]pyridine-2-carboxamide: (2E)-1-(4-acetyl-1-piperazinyl)-3-[4-[[2-(1-methylethyl)phenyl]thio]-3-nitrophenyl]-2-propen-1-one; and N-(3-hydroxypropyl)-5-methyl-1-[-4-[3-(trifluoromethyl)phenyl)]-2-thiazolyl]-1H-pyrazole-4-carboxamide.

In summary, this disclosure demonstrate the identification of ICAM-1 as an efficient TNBC therapeutic and diagnostic target based on the in vitro evaluation of its TNBC specific molecular profile and preclinical in vivo ICAM-1 targeted molecular MR imaging in a TNBC tumor model. The findings provide a rationale for further preclinical and clinical evaluation and development of ICAM-1 targeted treatments for TNBC.

Materials and Methods

4% formaldehyde solution, human GPCR signaling pathway finder RT2 profiler PCR array (SABiosciences, cat #PAHS-071Z), $RT^2$ first strand kit (SABiosciences, cat #C-03). $RT^2$ SYBR green/fluorescein qPCR master mix (SABiosciences, cat #PA-011), Qiagen RNeasy minikit were purchased from Qiagen (Valencia, CA, USA). Breast cancer tissue arrays (BR1503b, BR1505, and T088) were purchased from US Biomax (Rockville, MD, USA). Dulbecco's phosphate buffered saline (PBS), 4',6-diamidino-2-phenylindole (DAPI), Quant-iT™ RNA Assay Kit, 0.25% trypsin/2.6 mM ethylenediaminetetraacetic acid (EDTA) solution, Gibco® Dulbecco's Modified Eagle Medium (DMEM), Gibco®DMEM/F12(1:1) Roswell Park Memorial Institute (RPMI)-1640 Medium, McCoy-5A Medium were purchased from Invitrogen (Carlsbad, CA, USA). MEGM™ Mammary Epithelial Cell Growth Medium was purchased from Lonza (Allendale. NJ, USA)/Quantum Simply Cellular microbeads were purchased from Bangs Laboratory (Fishers, IN, USA). Mouse anti-human ICAM-1 monoclonal antibody (aICAM-1), immunoglobulin G (IgG) isotype control, and NorthernLight® 557 (NL557)-conjugated donkey anti-mouse IgG were purchased from R&D Systems (Minneapolis, MN, USA). Phycoerythrin (PE)-conjugated mouse anti-human ICAM-1 antibody (PE-aCXCR4) and PE-conjugated mouse IgG isotype (PE-IgG) were purchased from BioLegend (San Diego, CA, USA). 1-Ethyl-3-(3-dimethylaminopropyl) carbodiimide hydrochloride (EDC), N-hydroxysuccinimide (NHS), bovine serum albumin (BSA), anhydrous dimethyl sulfoxide (DMSO), Fluorescein isothiocyanate(FITC), Nanosep 300 k Omega centrifugal device were purchased from Sigma-Aldrich (St. Louis, MO, USA). Lab-Tek II Chamber Slide System was obtained from Thermo Fisher Scientific (Pittsburgh, PA, USA). Fluorogel with tris buffer was purchased from Electron Microscopy Sciences (Hatfield, PA, USA). Activation Buffer and Coupling Buffer was purchased from Ocean Nanotech (Springdale, AR, USA).

PCR Array

Human GPCR signaling pathwayfinder RT2 profiler PCR array was utilized to screen possible TNBC targets in MDA-MB-231, MCF7, and MCF10A cells. First, each cell line was incubated at $3\times10^5$ cells/well in 6-well cell culture plate overnight. 1 μg RNA of each cell line was converted to cDNA using the $RT^2$ first strand kit according to manufacturer's instructions. Diluted cDNA was added to the $RT^2$ SYBR green/fluorescein qPCR master mix. Human GPCR signaling pathwayfnder RT2 profiler PCR array was loaded with 25 μl/well of cDNA-master mix according to the PCR protocol provided by manufacturer. Results were analyzed using $RT^2$ Profiler PCR Array Data Analysis Template v3.0.

Immunohistological Staining 163 cases human breast cancer tissue microarray samples were evaluated for ICAM-1 expression. Immunohistochemical staining was performed by using paraffin-embedded human breast cancer tissue microarrays (BR1503B, BR1505, and T088 from US Biomax). The individual tissue cores in the microarrays were scored by a surgical pathologist, with no knowledge of sample identity, for no staining (0), weak staining (1), moderate staining (2), or strong staining (3). Photomicrographs were taken on an Olympus BX41 microscope by using an Olympus Q-color5 digital camera (Olympus America Inc, Chelmstord, MA).

Cell Culture

Three human triple-negative breast cancer (TNBC) cell lines (MDA-MB-231, MDA-MB-436, and MDA-MB-157); four human non-TNBC cell lines (MCF7, HCC1500, SKBR3, and MDA-MB-361); and two non-neoplastic mammary epithelial cell lines (AG11132 and MCF10A) were studied. MDA-MB-231, MDA-MB-436, and MDA-MB-157. MCF7, HCC1500, SKBR3, MDA-MB-361, and MCF10A were available through American Type Culture Collection (ATCC, Manassas. VA, USA); AG11132 was obtained from Coriell Institute (Camden, NJ, USA). MDA-MB-231, MDA-MB-436, MDA-MB-157, MCF7, MDA-MB-361 were cultured in DMEM Medium; HCC1500 in RPMI-1640 Medium; SKBR3 in McCoy-5A Medium; AG11132 in Mammary Epithelial Cell Basal Medium; MCF10A in DMEM/F12 (1:1) Medium, with each recommended supplements, respectively. All cells were maintained at 37° C. in a humidified incubator with 5% $CO_2$.

Quantification of ICAM-1 Gene Expression.

Gene expression level of ICAM-1 of breast cancer cell lines was characterized using qRT-PCR. MDA-MB-231, MDA-MB-436, MDA-MB-157. MCF7, HCC1500, MDA-MB-361, SKBR3, AG11132 and MCF10A cells were cultured at 3×105 cells/well in 6-well cell culture plate overnight. Then, cells were removed from each well by incubating with a trypsin/EDTA solution for 3 min. The cells were washed with PBS 3 times. RNA was extracted, purified using the Qiagen RNeasy minikit, and quantified by SpectraMaxPlus 384 UV-Visible Spectrophotometer (Molecular Devices Corp., Sunnyvale, CA, USA). Reverse transcription was conducted using the Applied Biosystems Taqman RT protocol. Detection and quantification of mRNA was performed by the StepOnePlus Real-Time PCR System (Applied Biosystems, Carlsbad, CA, USA). All PCR samples were referenced to the gene expression of Glyceraldehyde 3-phosphate dehydrogenase (GAPDH).

Quantification of ICAM-1 Surface Expression

Breast cancer cell ICAM-1 surface protein expression was evaluated by a BD FACSCalibur Flow Cytometer (BD Biosciences, San Jose, CA, USA). Quantification of the ICAM-1 density on the cell surface was determined with reference to Quantum Simply Cellular microbeads, using the protocol as provided by the manufacturer. Briefly, 106 cells were collected and rinsed twice through suspension-spin cycles. Cells were blocked by 1% bovine serum albumin (BSA) in PBS for 30 min in an ice bath. After BSA blockage, cells were incubated with PE-aICAM-1 antibody for 1 h at RT. Cells were rinsed with 1% BSA in PBS three times, resuspended in PBS, and evaluated by flow cytometry.

ICAM-1 Immunofluorescent Staining

MDA-MB-231, MDA-MB-436, MDA-MB-157, MCF7, HCC1500, MDA-MB-361, SKBR3. AG11132 and MCF10A (2×105 cells) were seeded in a Lab-Tek II Chamber Slide System separately with 2 mL medium overnight at 37° C. After medium was removed, cells were rinsed with PBS three times and fixed with 4% formaldehyde in PBS at RT for 10 min, and followed by washing with PBS. Then samples were blocked with 1% BSA in PBS for 30 min in an ice bath. After BSA blocking, samples were stained with aICAM-1 (primary antibody) for 1 h and rinsed with PBS. Samples were then incubated with NorthernLight® 557 conjugated goat anti-mouse secondary antibody (NL557 Abs) for another 1 h followed by washing with PBS. DAPI was used to stain the cell nucleus. Immunofluorescent stained samples were dried overnight in the dark and used for fluorescent microscope imaging. Samples were examined under a Leica TCS SP5 confocal fluorescent microscope (Leica Microsystems, Buffalo Grove, IL, USA). Digital images were captured with AxioVision digital image processing software.

Synthesis of ICAM-IO, HER2-IO and IGG-IO

Casein coated iron oxide nanoparticles (CNIO) were prepared as described previously [13] and stocked at a concentration of 5 mg/mL in PBS. 200 μL stock CNIO solution (1 mg) was mixed with 200 μL Activation Buffer (Ocean Nanotech, San Diego, CA), 50 μg EDC and 25 μg NHS for 20 min at RT. Then 100 μg ICAM-1 antibody or HER2 antibody or the IgG control and 400 μL Coupling Buffer (Ocean Nanotech, San Diego, CA) was added to CNIO solution and reacted for 2 h at RT with continuous mixing. As-synthesized ICAM-1-IOs or HER2-IOs or IGG-IOs were purified by ultra-centrifugation using Nanosep 300 k Omega centrifugal device.

Characterization of ICAM-IO

The morphology and size of ICAM-IO nanoparticles were studied using transmission electron microscope (TEM, Hitachi H-7500, accelerating voltage 75 kV). Typically, the TEM samples are prepared by dropping diluted nanoparticle solutions on the carbon coated copper grid and air-dried. The hydrodynamic size and surface charges of NPs in aqueous solution were evaluated using a dynamic light scattering (DLS) instrument (Malvern Zeta Sizer Nano S-90) equipped with a 22 mW He—Ne laser operating at 632.8 nm. PE-conjugated ICAM-IOs, or IGG-IOs, or HER2-IOs were also prepared to evaluate the antibody densities on obtained MRI probes. PE-conjugated IgG, or HER2 antibody, ICAM-1 antibody was used in the synthesis by replacing their non-fluorophore tagged forms. Other conditions were kept the same during the synthesis. Antibody density on each type of MR1 probes was calculated by using a PE standard concentration curve.

In Vitro Nanoparticle Binding

FTIC conjugated ICAM-IOs, or IGG-IOs, or HER2-IOs (ICAM-IO-FITC, or IGG-IO-FITC, or HER2-FITC-IO) were prepared to evaluate their in vitro TNBC targeting by flow cytometry. FITC was first conjugated to the casein coated on CNIOs according to FITC manufacturer's protocol. Then obtained FITC-CNIOs were conjugated with IGG, or HER2 antibody or ICAM-1 antibody as described in JCAM-IO synthesis.

Quantitative analysis of ICAM-IO-FITC binding to TNBCs (MDA-MB-231, MDA-MB-436, MDA-MB-157) were conducted using flow cytometry. Non-TNBCs (MCF7, HCC1500, MDA-MB-361, and SKBR3) and non-neoplastic cells (AG11132 and MCF10A) were selected as controls. Cells were seeded in 6-well plates (3×105 cells/well) and allowed to adhere overnight. Then cells were incubated for 4 h at 37° C. with (1) IGG- IO-FITC, (2) HER2-IO-FITC, and (3) ICAM-1-IO-FITC. The nanoparticle concentration used was 100 μg/mL. All nanoparticle treated cells were washed with PBS, harvested using a 0.25% trypsin/2.6 mM EDTA solution, and washed with PBS (pH 7.4) three times. Binding data were acquired using a BD FACSCalibur flow cytometer and analyzed using FlowJo software. The increase binding value was calculated by dividing the mean fluorescence intensity of HER2-1-FITC, or ICAM-1-IO-FITC stained cells by that of the non-specific IGG-IO-FITC stained cells.

Prussian Blue Staining

Nine cell lines (2×105 cells) were seeded in a Lab-Tek II Chamber Slide System separately with 1 mL medium overnight at 37° C. After medium was removed, cells were rinsed with PBS three times and fixed with 4% formaldehyde in PBS at RT for 10 min, and followed by washing with PBS, then soaked into working solution composed of 10% potassium ferrocyanide (II) trihydrate and 20% HCl solution (v:v=1:1) at 37° C. for 4 hours. After washed with PBS, slices were counterstained with nuclear fast red for 5 min.

Blue dots represents the remained IONPs in organs were investigated with a Leica TCS SP5 confocal fluorescent microscope (Leica Microsystems, Buffalo Grove. IL).

In Vivo MRI

Subcutaneous breast tumors were established by injecting 5×106 MDA-MB-231 cells into the fourth mammary fat pad of Nude mice (Charles River, Wilmington, MA) with n=5 for each group. Tumors were well developed for 5-7 weeks until the tumors were at least 200 mm3 in volume. In vivo MRI was performed on the tumor-bearing mice in three groups, which injected intravenously with IGG-IO, HER2-IO and ICAM-IO (at the dosage of 20 mg Fe/kg mouse weight), respectively. Images were obtained at pre- and 24 h post-injection using a 3 T MRI scanner (Siemens Healthcare (Malvern, PA, USA) with fast spin echo and multi-TE sequence for T2-weighted MRI. The imaging parameters included: TR of 3200 ms, TE of 86 ms, matrix of 320×128, field of view (FOV) of 120×60 mm2, flip angle of 150°, and slice thickness of 1.00 mm for T2-weighted imaging; TR of 3710 ms and 20 different TEs, starting at 12 ms with increments of 12 ms for multi-TE imaging. To quantity the signal intensity for tumor, ROIs were drawn around the whole tumor at the same slice with the same imaging depth. The pixel intensity was calculated and normalized to the area of ROIs by ImageJ software. The organs (liver, spleen, kidney, lung, heart, and muscle) and tumor samples were collected at 48 h after injection. Phenanthroline colorimetric method was used to determine the iron concentration in organs after the organs were digested in concentrated HNO3. Pathologies of MDA-MB-231 tumors with IGG-IO, or HER2-IO, or ICAM-IO were investigated by Hematoxylin&eosin (H&E) staining, Prussian blue staining, ICAM-1and HER2 immunohistological staining. All staining were performed for the tumor slices following the standard protocol.

Statistical Analysis

Quantitative data are presented as means±standard deviation. Differences were compared using unpaired t-test. When P-value were 0.05 or less, differences were considered statistically significant.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

TABLE 2

List of gene symbols.

| Symbol | Description |
|---|---|
| ADCY5 | Adenylate cyclase 5 |
| ADORA2A | Adenosine A2a receptor |
| ADRB1 | Adrenergic, beta-1-, receptor |
| ADRB2 | Adrenergic, beta-2-, receptor, surface |
| AGT | Angiotensinogen (serpin peptidase inhibitor, clade A, member 8) |
| AGTR1 | Angiotensin II receptor, type 1 |
| AGTR2 | Angiotensin II receptor, type 2 |
| AGTRAP | Angiotensin II receptor-associated protein |
| AKT1 | V-akt murine thymoma viral oncogene homolog 1 |
| ARRB1 | Arrestin, beta 1 |
| ARRB2 | Arrestin, beta 2 |
| BAI1 | Brain-specific angiogenesis inhibitor 1 |
| BCL2 | B-cell CLL/lymphoma 2 |
| BCL2L1 | BCL2-like 1 |
| CALCR | CALCITONIN RECEPTOR |
| CALCRL | Calcitonin receptor-like |
| CASR | Calcium-sensing receptor |
| CCL2 | Chemokine (C-C motif) ligand 2 |
| CCL4 | Chemokine (C-C motif) ligand 4 |
| CCND1 | Cyclin D1 |
| CCNE1 | Cyclin B1 |
| CCNE2 | Cyclin E2 |
| CDKN1A | Cyclin-dependent kinase inhibitor 1A (p21, Cip1) |
| CDKN1B | Cyclin-dependent kinase inhibitor 1B (p27, Kip1) |
| CFLAR | CASP8 and FADD-like apoptosis regulator |
| COL1A1 | Collagen, type I, alpha 1 |
| CRHR1 | Corticotropin releasing hormone receptor 1 |
| CRHR2 | Corticotropin releasing hormone receptor 2 |
| CTGF | Connective tissue growth factor |
| CYP19A1 | Cytochrome P450, family 19, subfamily A, polypeptide 1 |
| DRD1 | Dopamine receptor D1 |
| DRD2 | Dopamine receptor D2 |
| DUSP14 | Dual specificity phosphatase 14 |
| S1PR1 | Sphingosine-1-phosphate receptor 1 |
| LPAR1 | Lysophosphatidic acid receptor 1 |
| S1PR3 | Sphingosine-1-phosphate receptor 3 |
| LPAR2 | Lysophosphatidic acid receptor 2 |
| S1PR2 | Sphingosine-1-phosphate receptor 2 |
| EDN1 | Endothelin 1 |
| EGR1 | Early growth response 1 |
| ELK1 | ELK1, member of ETS oncogene family |
| ELK4 | ELK4, ETS-domain protein (SRF accessory protein 1) |
| FGF2 | Fibroblast growth factor 2 (basic) |
| FOS | FBJ murine osteosarcoma viral oncogene homolog |
| GALR2 | GALANIN RECEPTOR 2 |
| GCGR | Glucagon receptor |
| GNAQ | Guanine nucleotide binding protein (G protein), q polypeptide |
| GNAS | GNAS complex locus |
| GRM1 | Glutamate receptor, metabotropic 1 |
| GRM2 | Glutamate receptor, metabotropic 2 |
| GRM4 | Glutamate receptor, metabotropic 4 |
| GRM5 | Glutamate receptor, metabotropic 5 |
| GRM7 | Glutamate receptor, metabotropic 7 |
| ICAM1 | Intercellular adhesion molecule 1 |
| IL1B | Interleukin 1, beta |
| IL1R1 | Interleukin 1 receptor, type I |
| IL1R2 | Interleukin 1 receptor, type II |
| IL2 | Interleukin 2 |
| JUN | Jun proto-oncogene |
| JUNB | Jun B proto-oncogene |
| LHCGR | Luteinizing hormone/choriogonadotropin receptor |
| MAX | MYC associated factor X |
| MMP9 | Matrix metallopeptidase 9 (gelatinase B, 92 kDa gelatinase, 92 kDa type IV collagenase) |
| MYC | V-myc myelocytomatosis viral oncogene homolog (avian) |
| NOS2 | Nitric oxide synthase 2, inducible |
| OPRD1 | Opioid receptor, delta 1 |
| OPRK1 | Opioid receptor, kappa 1 |
| PDPK1 | 3-phosphoinositide dependent protein kinase-1 |
| PIK3CG | Phosphoinositide-3-kinase, catalytic, gamma polypeptide |
| PRKCA | Protein kinase C, alpha |
| PTGDR | Prostaglandin D2 receptor (DP) |
| PTGS2 | Prostaglandin-endoperoxide synthase 2 (prostaglandin G/H synthase and cyclooxygenase) |
| PTH1R | Parathyroid hormone 1 receptor |
| RGS2 | Regulator of G-protein signaling 2, 24 kDa |
| RHO | Rhodopsin |
| SCTR | Secretin receptor |
| SERPINE1 | Serpin peptidase inhibitor, clade E (nexin, plasminogen activator inhibitor type 1), member 1 |
| SOCS1 | Suppressor of cytokine signaling 1 |

TABLE 2-continued

List of gene symbols.

| Symbol | Description |
|---|---|
| TNF | Tumor necrosis factor |
| TSHR | Thyroid stimulating hormone receptor |
| UCP1 | Uncoupling protein 1 (mitochondrial, proton carrier) |
| VCAM1 | Vascular cell adhesion molecule 1 |
| VEGFA | Vascular endothelial growth factor A |
| YWHAZ | Tyrosine 3-monooxygenase/tryptophan 5-monooxygenase activation protein, zeta polypeptide |
| B2M | Beta-2-microglobulin |
| HPRT1 | Hypoxanthine phosphoribosyltransferase 1 |
| RPL13A | Ribosomal protein L13a |
| GAPDH | Glyceraldehyde-3-phosphate dehydrogenase |
| ACTB | Actin, beta |
| HGDC | Human Genomic DNA Contamination |
| RTC | Reverse Transcription Control |
| PPC | Positive PCR Control |

What is claimed is:

1. A method of treating triple negative breast cancer (TNBC) in a patient, the method comprising administering enlimomab to the patient, wherein administering the enlimomab reduces TNBC cell migration in the patient.

2. The method of claim 1, wherein the patient is a human patient.

3. The method of claim 1, wherein the TNBC of the patient comprises a mutation in the BRCA1 gene.

4. The method of claim 1, wherein ICAM-1 is expressed by TNBC cells of the patient.

5. The method of claim 1, wherein ICAM-1 is expressed on the surface of TNBC cells of the patient.

* * * * *